(12) United States Patent
Mori et al.

(10) Patent No.: US 7,534,590 B2
(45) Date of Patent: May 19, 2009

(54) METHOD FOR PRODUCING MONATIN

(75) Inventors: Ken-ichi Mori, Kawasaki (JP);
Masakazu Sugiyama, Kawasaki (JP);
Tadashi Takemoto, Kawasaki (JP)

(73) Assignee: AJINOMOTO Co., Inc., Tokyo (JP)

( * ) Notice: Subject to any disclaimer, the term of this patent is extended or adjusted under 35 U.S.C. 154(b) by 385 days.

(21) Appl. No.: 11/317,308

(22) Filed: Dec. 27, 2005

(65) Prior Publication Data
US 2006/0154343 A1    Jul. 13, 2006

Related U.S. Application Data

(63) Continuation of application No. PCT/JP2004/009373, filed on Jun. 25, 2004.

(30) Foreign Application Priority Data

Jun. 26, 2003    (JP)    ............... 2003-183291

(51) Int. Cl.
 C12P 13/04    (2006.01)
 C12P 13/12    (2006.01)
 C12P 13/22    (2006.01)
 C12P 17/10    (2006.01)
 C07D 209/18    (2006.01)

(52) U.S. Cl. ............ 435/106; 435/108; 435/113; 435/121; 548/495

(58) Field of Classification Search ............ None
See application file for complete search history.

(56) References Cited

U.S. PATENT DOCUMENTS

| 5,994,559 | A | 11/1999 | Abushanab et al. |
| 6,613,933 | B1 | 9/2003 | Nagashima et al. |
| 7,297,800 | B2 | 11/2007 | Sugiyama et al. |
| 7,402,412 | B2 * | 7/2008 | Sugiyama et al. ............ 435/110 |
| 2005/0020508 | A1 | 1/2005 | Amino et al. |
| 2005/0272939 | A1 | 12/2005 | Amino et al. |
| 2006/0154343 | A1 | 7/2006 | Mori et al. |
| 2007/0072277 | A1 | 3/2007 | Sugiyama et al. |

FOREIGN PATENT DOCUMENTS

| JP | 61-178948 | 8/1986 |
| JP | 61-178953 | 8/1986 |
| JP | 63-267287 | 4/1988 |
| JP | 11-171895 | 6/1999 |
| JP | 2000-125896 | 5/2000 |
| JP | 2003-171365 | 6/2003 |

OTHER PUBLICATIONS

D. de Jesus, et al., "Diastereoselective Formation of a Quaternary Center in a Pyroglutamate Derivative. Formal Synthesis of Monatin", Tetrahedron Letters, vol. 42, 2001, pp. 6793-6796.
K. Nakamura, et al., "Total Synthesis of Monatin", Organic Letters, vol. 2, No. 19, 2000, pp. 2967-2970.
C.W. Holzapfel, et al., "A Simple Cycloaddition Approach to a Racemate of the Natural Sweetener Monatin", Synthetic Communications, vol. 24, No. 22, 1994, pp. 3197-3211.
C.W. Holzapfel, et al., The Synthesis of a Gamma-Keto-Alpha-Amino Acid, A Key Intermediate in the Synthesis of Monatin, A New Natural Sweetener, Synthetic Communications, vol. 23, No. 18, 1993, pp. 2511-2526.
U.S. Appl. No. 12/108,889, filed Apr. 24, 2008, Sugiyama et al.

* cited by examiner

Primary Examiner—Herbert J. Lilling
(74) Attorney, Agent, or Firm—Oblon, Spivak, McClelland, Maier & Neustadt, P.C.

(57) ABSTRACT

A solution to be treated containing monatin and impurities is treated with a nonpolar resin having aromatic rings, whereby monatin is separated from the solution. Treatment with the nonpolar resin having aromatic rings results in efficient separation of monatin under a mild pH condition.

10 Claims, 1 Drawing Sheet

SEQUENCE LISTING

```
<160> NUMBER OF SEQ ID NOS: 13

<210> SEQ ID NO 1
<211> LENGTH: 1296
<212> TYPE: DNA
<213> ORGANISM: Pseudomonas taetrolens
<220> FEATURE:
<221> NAME/KEY: CDS
<222> LOCATION: (444)..(1118)
<223> OTHER INFORMATION: aldolase 2
<220> FEATURE:
<221> NAME/KEY: CDS
<222> LOCATION: (456)..(1118)
<223> OTHER INFORMATION: aldolase 1

<400> SEQUENCE: 1
gtacaccgtc ctgactcagg gcgcgctcgg cacgggttga tctatgagcg ctgtttgccc     60
agaatgacgt cggggtcacg tacgatcaaa gcaactacct gatcgcccag tgggcctgac    120
ctgtccggtg tcggcatcag ctacctgcct cgccaagtgt ctctcgccat tggtggacca    180
gggtcgggct actagtcatc gaaaccgagc ctgcgctgcc tcccatccaa tacatcgccg    240
tacaccgcgc cgatcgtctt cagggcctca gcgtcgaggt tgcacgtctg gcagctcgtt    300
gctgtgattt cagccgcatg gtgtggtaac acaggcgctg gatacgagaa aaaaagcgat    360
gtattttcat agataaatat cgctaatagt gccaagcgac ctttcttact atgaacgcat    420
agcccacaag ggttcagtca ttc atg gag gtc gct atg tca ttg ccc ggt tca    473
                         Met Glu Val Ala Met Ser Leu Pro Gly Ser
                           1               5                  10 cgc atc tac cct tct ccg ccc cag gca cca cgc tca ctg ctg gac gcg    521
Arg Ile Tyr Pro Ser Pro Pro Gln Ala Pro Arg Ser Leu Leu Asp Ala
               15                  20                  25 ttt cag aac gta gtg acg ccg cat atc agt gat aac ctc ggg cgt cac    569
Phe Gln Asn Val Val Thr Pro His Ile Ser Asp Asn Leu Gly Arg His
           30                  35                  40 atc ggt gcc cgg ggg ctg acg cgc tat aac cac acc ggc aaa ctg gtg    617
Ile Gly Ala Arg Gly Leu Thr Arg Tyr Asn His Thr Gly Lys Leu Val
       45                  50                  55
```

```
ggc acc gcc ctg acg gtg aag act cgc ccc ggc gac aac ctc tac atc      665
Gly Thr Ala Leu Thr Val Lys Thr Arg Pro Gly Asp Asn Leu Tyr Ile
    60                  65                  70 tac aaa gca ctg acg ctg atc gaa ccc gga cac gtg ctg gtg atc gac      713
Tyr Lys Ala Leu Thr Leu Ile Glu Pro Gly His Val Leu Val Ile Asp
75                  80                  85                  90 gct cag ggt gac gcg acc aac gcg gtc att ggt gag ctg atc aag ctc      761
Ala Gln Gly Asp Ala Thr Asn Ala Val Ile Gly Glu Leu Ile Lys Leu
                95                  100                 105 tac gcg cag caa cgt ggc tgt gtc ggc ttc gtc gtc gac ggc gcc atc      809
Tyr Ala Gln Gln Arg Gly Cys Val Gly Phe Val Val Asp Gly Ala Ile
            110                 115                 120 cgc gat gtc gcc agt ttt gaa gat acg cct tgc tat gcc cgt agc gtg      857
Arg Asp Val Ala Ser Phe Glu Asp Thr Pro Cys Tyr Ala Arg Ser Val
        125                 130                 135 gtg cat tgc ggt ccc tac aaa agc ggc cca ggg gaa atc aat gtc ccg      905
Val His Cys Gly Pro Tyr Lys Ser Gly Pro Gly Glu Ile Asn Val Pro
    140                 145                 150 gtg tca atc ggc ggg atg atc atc aat ccg ggc gac atc att gtc ggt      953
Val Ser Ile Gly Gly Met Ile Ile Asn Pro Gly Asp Ile Ile Val Gly
155                 160                 165                 170 gac gag gat ggg ctg gtt gcc ttc tcg ccc gac cat gcc gag cag gtg     1001
Asp Glu Asp Gly Leu Val Ala Phe Ser Pro Asp His Ala Glu Gln Val
                175                 180                 185 ttg gtc aag gcg cga gag cat gac gcg cat gaa cag cag gtc aaa gcc     1049
Leu Val Lys Ala Arg Glu His Asp Ala His Glu Gln Gln Val Lys Ala
            190                 195                 200 gaa atc gcc act ggc gcc atc gat cag tca tgg ctg gac aaa gtg ctg     1097
Glu Ile Ala Thr Gly Ala Ile Asp Gln Ser Trp Leu Asp Lys Val Leu
        205                 210                 215 gaa aag gct ggc ctg gcg aac      tgaaaacac tgtgtaatcg ccttgctgca    1148
Glu Lys Ala Gly Leu Ala Asn
        220             225 gcgacattgc tgtcggacag gatgatctga cgcttcagtt acgcgttctt gggtgcaccg   1208
cgccacgtca ggaagtggct gctgccgcat gcaggtgaca tgtcatgtac catggcagca   1268
gcacgtgaca tgcacgatgt gctcacgc                                      1296

<210> SEQ ID NO 2
<211> LENGTH: 225
<212> TYPE: PRT
<213> ORGANISM: Pseudomonas taetrolens

<400> SEQUENCE: 2

Met Glu Val Ala Met Ser Leu Pro Gly Ser Arg Ile Tyr Pro Ser Pro
1               5                   10                  15

Pro Gln Ala Pro Arg Ser Leu Leu Asp Ala Phe Gln Asn Val Thr
            20                  25                  30

Pro His Ile Ser Asp Asn Leu Gly Arg His Ile Gly Ala Arg Gly Leu
        35                  40                  45

Thr Arg Tyr Asn His Thr Gly Lys Leu Val Gly Thr Ala Leu Thr Val
    50                  55                  60

Lys Thr Arg Pro Gly Asp Asn Leu Tyr Ile Tyr Lys Ala Leu Thr Leu
65                  70                  75                  80

Ile Glu Pro Gly His Val Leu Val Ile Asp Ala Gln Gly Asp Ala Thr
                85                  90                  95

Asn Ala Val Ile Gly Glu Leu Ile Lys Leu Tyr Ala Gln Gln Arg Gly
            100                 105                 110
```

```
Cys Val Gly Phe Val Val Asp Gly Ala Ile Arg Asp Val Ala Ser Phe
            115                 120                 125

Glu Asp Thr Pro Cys Tyr Ala Arg Ser Val Val His Cys Gly Pro Tyr
    130                 135                 140

Lys Ser Gly Pro Gly Glu Ile Asn Val Pro Val Ser Ile Gly Gly Met
145                 150                 155                 160

Ile Ile Asn Pro Gly Asp Ile Ile Val Gly Asp Glu Asp Gly Leu Val
                165                 170                 175

Ala Phe Ser Pro Asp His Ala Glu Gln Val Leu Val Lys Ala Arg Glu
            180                 185                 190

His Asp Ala His Glu Gln Gln Val Lys Ala Glu Ile Ala Thr Gly Ala
        195                 200                 205

Ile Asp Gln Ser Trp Leu Asp Lys Val Leu Glu Lys Ala Gly Leu Ala
210                 215                 220

Asn
225

<210> SEQ ID NO 3
<211> LENGTH: 221
<212> TYPE: PRT
<213> ORGANISM: Pseudomonas taetrolens

<400> SEQUENCE: 3

Met Ser Leu Pro Gly Ser Arg Ile Tyr Pro Ser Pro Gln Ala Pro
1               5                   10                  15

Arg Ser Leu Leu Asp Ala Phe Gln Asn Val Val Thr Pro His Ile Ser
            20                  25                  30

Asp Asn Leu Gly Arg His Ile Gly Ala Arg Gly Leu Thr Arg Tyr Asn
        35                  40                  45

His Thr Gly Lys Leu Val Gly Thr Ala Leu Thr Val Lys Thr Arg Pro
    50                  55                  60

Gly Asp Asn Leu Tyr Ile Tyr Lys Ala Leu Thr Leu Ile Glu Pro Gly
65                  70                  75                  80

His Val Leu Val Ile Asp Ala Gln Gly Asp Ala Thr Asn Ala Val Ile
                85                  90                  95

Gly Glu Leu Ile Lys Leu Tyr Ala Gln Gln Arg Gly Cys Val Gly Phe
            100                 105                 110

Val Val Asp Gly Ala Ile Arg Asp Val Ala Ser Phe Glu Asp Thr Pro
        115                 120                 125

Cys Tyr Ala Arg Ser Val Val His Cys Gly Pro Tyr Lys Ser Gly Pro
    130                 135                 140

Gly Glu Ile Asn Val Pro Val Ser Ile Gly Gly Met Ile Ile Asn Pro
145                 150                 155                 160

Gly Asp Ile Ile Val Gly Asp Glu Asp Gly Leu Val Ala Phe Ser Pro
                165                 170                 175

Asp His Ala Glu Gln Val Leu Val Lys Ala Arg Glu His Asp Ala His
            180                 185                 190

Glu Gln Gln Val Lys Ala Glu Ile Ala Thr Gly Ala Ile Asp Gln Ser
        195                 200                 205

Trp Leu Asp Lys Val Leu Glu Lys Ala Gly Leu Ala Asn
    210                 215                 220

<210> SEQ ID NO 4
<211> LENGTH: 1176
<212> TYPE: DNA
```

<213> ORGANISM: Pseudomonas coronafaciens
<220> FEATURE:
<221> NAME/KEY: CDS
<222> LOCATION: (398)..(1141)
<223> OTHER INFORMATION: PcALD

<400> SEQUENCE: 4

| | | |
|---|---|---|
| gtcgtaaccc acaccgtgct tggcaatgat cttcagattg cctgaggcct ggatcatgtc | 60 |
| cttggtcagc ttgccttggc gcacgatgat cgcgtgaggt gttcgtcgc ggattattgc | 120 |
| agtcagctct tcggcgggca tgtagggcgt ggtggggatg atggtaatgc cttgagatgc | 180 |
| ggcgtaggcc atcgcatcgg ctgccagttc ggggcctgtc agcaggatct tccgattcat | 240 |
| gatcgatacc ttgttttat agaggtcgtg tgcggcgtcg agaagacatc tgcacctggc | 300 |
| tgaaccctac cataatgaaa tgtcgttgca atatagatga attgataatc ttgatgagtg | 360 |
| gtttttattt gggtatccgc ctattgatcc tgttaaa atg aaa tgt cat tct gtt | 415 |
|                                                         Met Lys Cys His Ser Val<br>                                                      1               5 | |
| att tgg ttt agt gcc tgg ccg cat cca ata att tca aga gag aaa agc<br>Ile Trp Phe Ser Ala Trp Pro His Pro Ile Ile Ser Arg Glu Lys Ser<br>                10                       15                     20 | 463 |
| cac atg acg atc gga ttc aga gtt ctc agt gca gcc cgc aaa gtc agc<br>His Met Thr Ile Gly Phe Arg Val Leu Ser Ala Ala Arg Lys Val Ser<br>     25                     30                     35 | 511 |
| ccg gaa tgg gtc gcc cgc tac cgc gat gtt ccg gtg gcc aat gtc agt<br>Pro Glu Trp Val Ala Arg Tyr Arg Asp Val Pro Val Ala Asn Val Ser<br>40                       45                     50 | 559 |
| gac tcg atg aac cgg atg acc gct ggc ggg tcc agg ctg cgc ccc atg<br>Asp Ser Met Asn Arg Met Thr Ala Gly Gly Ser Arg Leu Arg Pro Met<br>55                      60                     65                     70 | 607 |
| cac cgt gcg ggc gtt ctc gcc ggg ccg gcc ttg acg gtc aag gcc cgt<br>His Arg Ala Gly Val Leu Ala Gly Pro Ala Leu Thr Val Lys Ala Arg<br>                75                       80                     85 | 655 |
| ccg ggt gac aac ctg atg ctg cat tac gct att gat att gct cag ccg<br>Pro Gly Asp Asn Leu Met Leu His Tyr Ala Ile Asp Ile Ala Gln Pro<br>     90                     95                     100 | 703 |
| ggc gac gtg att gtg gtg gat gcc ggg ggc gac ctg act aac gcg ctg<br>Gly Asp Val Ile Val Val Asp Ala Gly Gly Asp Leu Thr Asn Ala Leu<br>105                    110                    115 | 751 |
| att ggc gaa atg atg gtg gct tat gct gta aaa cgt ggt gtg gct ggc<br>Ile Gly Glu Met Met Val Ala Tyr Ala Val Lys Arg Gly Val Ala Gly<br>120                    125                    130 | 799 |
| atc gtc atc aac ggc gcc atc cgt gat gcc gcc agc atc ggt gca ggc<br>Ile Val Ile Asn Gly Ala Ile Arg Asp Ala Ala Ser Ile Gly Ala Gly<br>135                    140                    145                    150 | 847 |
| gac ttc ccg atg ttt gca gcc ggt gta tcg cat cgg ggt cct tat aaa<br>Asp Phe Pro Met Phe Ala Ala Gly Val Ser His Arg Gly Pro Tyr Lys<br>                    155                    160                    165 | 895 |
| gac ggg cca ggc gaa atc aat gtc ccg atc gcc atc gac ggc atg gtc<br>Asp Gly Pro Gly Glu Ile Asn Val Pro Ile Ala Ile Asp Gly Met Val<br>                  170                     175                    180 | 943 |
| atc gag gcg ggg gat ctg gtg ata ggc gat gac gac ggc ttg ctg tgt<br>Ile Glu Ala Gly Asp Leu Val Ile Gly Asp Asp Asp Gly Leu Leu Cys<br>              185                    190                    195 | 991 |
| gtc cct tac gac cag gtt gca gag gtg tat gac cgg gca gca gcc aag<br>Val Pro Tyr Asp Gln Val Ala Glu Val Tyr Asp Arg Ala Ala Ala Lys<br>200                    205                    210 | 1039 |
| cat cat gca gag caa aag caa ctg gag cag atc gcc aag ggc gaa aat<br>His His Ala Glu Gln Lys Gln Leu Glu Gln Ile Ala Lys Gly Glu Asn<br>215                    220                    225                    230 | 1087 |

```
gat cgc tcc tgg gta ctt gaa tca ttg aag aaa aaa ggc tgc cag ctt      1135
Asp Arg Ser Trp Val Leu Glu Ser Leu Lys Lys Lys Gly Cys Gln Leu
                235                 240                 245 cca gaa tgagctggtg taatcgtgcc tttcgcgcac gatct                       1176
Pro Glu
```

<210> SEQ ID NO 5
<211> LENGTH: 248
<212> TYPE: PRT
<213> ORGANISM: Pseudomonas coronafaciens

<400> SEQUENCE: 5

```
Met Lys Cys His Ser Val Ile Trp Phe Ser Ala Trp Pro His Pro Ile
 1               5                  10                  15

Ile Ser Arg Glu Lys Ser His Met Thr Ile Gly Phe Arg Val Leu Ser
                20                  25                  30

Ala Ala Arg Lys Val Ser Pro Glu Trp Val Ala Arg Tyr Arg Asp Val
            35                  40                  45

Pro Val Ala Asn Val Ser Asp Ser Met Asn Arg Met Thr Ala Gly Gly
        50                  55                  60

Ser Arg Leu Arg Pro Met His Arg Ala Gly Val Leu Ala Gly Pro Ala
65                  70                  75                  80

Leu Thr Val Lys Ala Arg Pro Gly Asp Asn Leu Met Leu His Tyr Ala
                85                  90                  95

Ile Asp Ile Ala Gln Pro Gly Asp Val Ile Val Asp Ala Gly Gly
            100                 105                 110

Asp Leu Thr Asn Ala Leu Ile Gly Glu Met Met Val Ala Tyr Ala Val
        115                 120                 125

Lys Arg Gly Val Ala Gly Ile Val Asn Gly Ala Ile Arg Asp Ala
    130                 135                 140

Ala Ser Ile Gly Ala Gly Asp Phe Pro Met Phe Ala Ala Gly Val Ser
145                 150                 155                 160

His Arg Gly Pro Tyr Lys Asp Gly Pro Gly Glu Ile Asn Val Pro Ile
                165                 170                 175

Ala Ile Asp Gly Met Val Ile Glu Ala Gly Asp Leu Val Ile Gly Asp
            180                 185                 190

Asp Asp Gly Leu Leu Cys Val Pro Tyr Asp Gln Val Ala Glu Val Tyr
        195                 200                 205

Asp Arg Ala Ala Ala Lys His His Ala Glu Gln Lys Gln Leu Glu Gln
    210                 215                 220

Ile Ala Lys Gly Glu Asn Asp Arg Ser Trp Val Leu Glu Ser Leu Lys
225                 230                 235                 240

Lys Lys Gly Cys Gln Leu Pro Glu
                245
```

<210> SEQ ID NO 6
<211> LENGTH: 1709
<212> TYPE: DNA
<213> ORGANISM: Bacillus macerans
<220> FEATURE:
<221> NAME/KEY: CDS
<222> LOCATION: (630)..(1481)
<223> OTHER INFORMATION: BMDAT

<400> SEQUENCE: 6

```
tacatcaggt agcgccatgc atgacagaaa gggatcatga gcgttatctg ctgcgtttac     60
aacagagtga cgactgagtc agagcaattg tcgactttat cgcagaggtt tttatcagga    120
```

-continued

```
tcattatgcc atcagcttga gttgcaattc gaggatgcca tgtctggtca gacaacatta    180
aatccaggca ttgttagcta tgatgtcagt aaaggtggca gtttagtgat tagtatgcgc    240
tattctgtgt cctatccatt cgatgaaaaa ttacggaggc tcaacgttta gttgtaaaaa    300
gaggattttc attagatatt caagacgact ccaagcccca ttatgtcagt gaagatgatc    360
catttatcca acattagcg gctatttata gacgtcaatc aggagataca gaaacaccgt    420
tattatctac aggtggtgga acgtatgcac gtgtgctgaa aaaggcgtg gcctttggca    480 tgctattccc tggggagcag gatgtggcgc atcgggcgga tgagtttgta gtgattgaaa    540
atcttgtaaa agcagcggct atttatgcgg aagcaattgt tgagcttgcg ggaaaaaaat    600
aacataaaga cgaaaggat gaacggaaa atg gca tat tca tta tgg aat gat      653
                                Met Ala Tyr Ser Leu Trp Asn Asp
                                 1               5 caa att gtt gaa gaa gga tct att gca atc tca cca gaa gac aga ggt      701
Gln Ile Val Glu Glu Gly Ser Ile Ala Ile Ser Pro Glu Asp Arg Gly
         10                  15                  20 tat cag ttt ggt gac ggt att tat gaa gta att aaa gtt tat aac gga      749
Tyr Gln Phe Gly Asp Gly Ile Tyr Glu Val Ile Lys Val Tyr Asn Gly
 25                  30                  35                  40 aat atg ttt aca gca caa gag cac att gat cgt ttc tat gcg agc gcc      797
Asn Met Phe Thr Ala Gln Glu His Ile Asp Arg Phe Tyr Ala Ser Ala
                 45                  50                  55 gaa aaa att cgc ctt gtt atc cct tat aca aaa gat gtt tta cac aag      845
Glu Lys Ile Arg Leu Val Ile Pro Tyr Thr Lys Asp Val Leu His Lys
             60                  65                  70 tta cta cat gag cta att gaa aag aat aat cta gaa aca gga cat gtt      893
Leu Leu His Glu Leu Ile Glu Lys Asn Asn Leu Glu Thr Gly His Val
         75                  80                  85 tat ttt caa atc act cgt ggg gct aat tca cgt aat cac gtt ttc ccg      941
Tyr Phe Gln Ile Thr Arg Gly Ala Asn Ser Arg Asn His Val Phe Pro
 90                  95                 100 gat gca agt att cct gct gta tta act gga aat gta aaa gcg ggt gaa      989
Asp Ala Ser Ile Pro Ala Val Leu Thr Gly Asn Val Lys Ala Gly Glu
105                 110                 115                 120 cgt gca tat gaa aac ttt gaa aaa ggt gtt aaa gcc act ttt gtt gag     1037
Arg Ala Tyr Glu Asn Phe Glu Lys Gly Val Lys Ala Thr Phe Val Glu
                125                 130                 135 gat att cgt tgg ttg cgt tgt gac att aaa tct tta aac ttg ctt ggt     1085
Asp Ile Arg Trp Leu Arg Cys Asp Ile Lys Ser Leu Asn Leu Leu Gly
            140                 145                 150 gca gta tta gca aaa caa gaa gct gcg gag aaa ggt tgt tat gaa gcg     1133
Ala Val Leu Ala Lys Gln Glu Ala Ala Glu Lys Gly Cys Tyr Glu Ala
        155                 160                 165 atc tta cat cgc gga gat atc gtg aca gaa tgc tct tca gct aat gtt     1181
Ile Leu His Arg Gly Asp Ile Val Thr Glu Cys Ser Ser Ala Asn Val
    170                 175                 180 tac gga att aaa gat gga aaa ctt tat aca cat cca gct aat aat ttc     1229
Tyr Gly Ile Lys Asp Gly Lys Leu Tyr Thr His Pro Ala Asn Asn Phe
185                 190                 195                 200 atc tta aat ggt att aca cgt caa gtc att tta aaa tgt gcg gaa gaa     1277
Ile Leu Asn Gly Ile Thr Arg Gln Val Ile Leu Lys Cys Ala Glu Glu
                205                 210                 215 att aat tta cca gta atc gaa gag cca atg acg aaa gct gat tta cta     1325
Ile Asn Leu Pro Val Ile Glu Glu Pro Met Thr Lys Ala Asp Leu Leu
            220                 225                 230 aca atg gat gaa atc att gtg tcg tct gta tct tct gag gtt acg cca     1373
Thr Met Asp Glu Ile Ile Val Ser Ser Val Ser Ser Glu Val Thr Pro
```

```
                    235                 240                 245
gtc att gat gtg gac ggc aac caa att ggg gct gga gtt ccc ggt gaa      1421
Val Ile Asp Val Asp Gly Asn Gln Ile Gly Ala Gly Val Pro Gly Glu
    250                 255                 260 tgg act cgt caa tta cag caa tca ttt gaa gcg aaa tta cca ctt tca      1469
Trp Thr Arg Gln Leu Gln Gln Ser Phe Glu Ala Lys Leu Pro Leu Ser
265                 270                 275                 280 atg aat acc aaa taaagaacc ttgtagagaa ctatctgtat ggatagttct           1521
Met Asn Thr Lys ctttatttat gggtgtaatg ttgggtctcg tcatgtaaaa taaaaggat agtagaataa     1581 tcttacagat tgaaatttgt agagcaatgt cgatgtaatg aatacataag aatgcataga   1641 ctcttttac aaaggggatc gagaaaaaag agaactaaag agatggtaag taagaatgga    1701
gtgacctt                                                             1709

<210> SEQ ID NO 7
<211> LENGTH: 284
<212> TYPE: PRT
<213> ORGANISM: Bacillus macerans

<400> SEQUENCE: 7

Met Ala Tyr Ser Leu Trp Asn Asp Gln Ile Val Glu Glu Gly Ser Ile
 1               5                  10                  15

Ala Ile Ser Pro Glu Asp Arg Gly Tyr Gln Phe Gly Asp Gly Ile Tyr
            20                  25                  30

Glu Val Ile Lys Val Tyr Asn Gly Asn Met Phe Thr Ala Gln Glu His
        35                  40                  45

Ile Asp Arg Phe Tyr Ala Ser Ala Glu Lys Ile Arg Leu Val Ile Pro
    50                  55                  60

Tyr Thr Lys Asp Val Leu His Lys Leu Leu His Glu Leu Ile Glu Lys
65                  70                  75                  80

Asn Asn Leu Glu Thr Gly His Val Tyr Phe Gln Ile Thr Arg Gly Ala
                85                  90                  95

Asn Ser Arg Asn His Val Phe Pro Asp Ala Ser Ile Pro Ala Val Leu
            100                 105                 110

Thr Gly Asn Val Lys Ala Gly Glu Arg Ala Tyr Glu Asn Phe Glu Lys
        115                 120                 125

Gly Val Lys Ala Thr Phe Val Glu Asp Ile Arg Trp Leu Arg Cys Asp
    130                 135                 140

Ile Lys Ser Leu Asn Leu Leu Gly Ala Val Leu Ala Lys Gln Glu Ala
145                 150                 155                 160

Ala Glu Lys Gly Cys Tyr Glu Ala Ile Leu His Arg Gly Asp Ile Val
                165                 170                 175

Thr Glu Cys Ser Ser Ala Asn Val Tyr Gly Ile Lys Asp Gly Lys Leu
            180                 185                 190

Tyr Thr His Pro Ala Asn Asn Phe Ile Leu Asn Gly Ile Thr Arg Gln
        195                 200                 205

Val Ile Leu Lys Cys Ala Glu Glu Ile Asn Leu Pro Val Ile Glu Glu
    210                 215                 220

Pro Met Thr Lys Ala Asp Leu Leu Thr Met Asp Glu Ile Ile Val Ser
225                 230                 235                 240

Ser Val Ser Ser Glu Val Thr Pro Val Ile Asp Val Asp Gly Asn Gln
                245                 250                 255

Ile Gly Ala Gly Val Pro Gly Glu Trp Thr Arg Gln Leu Gln Gln Ser
            260                 265                 270
```

-continued

```
Phe Glu Ala Lys Leu Pro Leu Ser Met Asn Thr Lys
        275                 280

<210> SEQ ID NO 8
<211> LENGTH: 1424
<212> TYPE: DNA
<213> ORGANISM: Bacillus sphaericus
<220> FEATURE:
<221> NAME/KEY: CDS
<222> LOCATION: (427)..(1275)
<223> OTHER INFORMATION: BSDAT

<400> SEQUENCE: 8
acaaggagga tccgttaatc aaacgttag ctggtgttta tcgccgacaa acgggcgata      60
acgaaacacc tttactttca acaggcggtg gaacgtatgc acgcgtcttg aaaaaaggtg    120
tggcattcgg catgctttc cctggtgatc agatgtcat gcatcgtgcg gatgaatatg     180
taattgttga taaattagta caagctgctg ctatttatgc agaagccatt gcagaactgg    240
ctgggaagta agtgtcatta agagcgtaat gttttcttgc aaagagatc acgaagcttc    300 acacgccaag cacttcactg aaaatctac tttgatttac tgcatctggt cttacttgat   360
cgtctagtgg gaatcattgt acttaaaaat gtgaaaataa cttaaaaatg aaaaggatgt    420 ataaac atg gca tac tca tta tgg aat gac caa atc gtt gaa gaa gga      468
       Met Ala Tyr Ser Leu Trp Asn Asp Gln Ile Val Glu Glu Gly
           1               5                  10 tct att aca att tca cca gaa gac cgt ggt tat caa ttt ggt gat ggt     516
Ser Ile Thr Ile Ser Pro Glu Asp Arg Gly Tyr Gln Phe Gly Asp Gly
 15              20                 25                  30 att tac gaa gta atc aaa gta tat aac ggg cat atg ttt aca gca caa     564
Ile Tyr Glu Val Ile Lys Val Tyr Asn Gly His Met Phe Thr Ala Gln
             35                  40                  45 gag cac atc gat cgt ttc tat gct agt gcc gaa aaa att cgc ctt gtt     612
Glu His Ile Asp Arg Phe Tyr Ala Ser Ala Glu Lys Ile Arg Leu Val
         50                  55                  60 att cct tat aca aaa gat gta tta cac aaa tta ttg cat gat tta atc     660
Ile Pro Tyr Thr Lys Asp Val Leu His Lys Leu Leu His Asp Leu Ile
     65                  70                  75 gaa aaa aat aat tta aat aca ggt cat gtt tac ttc caa att aca cgt     708
Glu Lys Asn Asn Leu Asn Thr Gly His Val Tyr Phe Gln Ile Thr Arg
 80                  85                  90 gga aca act tct cgt aac cac att ttc ccg gat gca agc gta cca gca     756
Gly Thr Thr Ser Arg Asn His Ile Phe Pro Asp Ala Ser Val Pro Ala
 95                 100                 105                 110 gtg cta aca ggt aat gtt aaa act ggt gaa cgt tca att gaa aat ttc     804
Val Leu Thr Gly Asn Val Lys Thr Gly Glu Arg Ser Ile Glu Asn Phe
            115                 120                 125 gaa aaa ggc gta aaa gcg aca ttg gtt gaa gat gtt cgt tgg tta cgt     852
Glu Lys Gly Val Lys Ala Thr Leu Val Glu Asp Val Arg Trp Leu Arg
        130                 135                 140 tgt gat att aaa tct tta aat tta ctt ggc gcg gta ctt gcg aaa caa     900
Cys Asp Ile Lys Ser Leu Asn Leu Leu Gly Ala Val Leu Ala Lys Gln
    145                 150                 155 gaa gca tct gaa aaa ggt tgt tac gaa gcc att tta cac cgt gga gat     948
Glu Ala Ser Glu Lys Gly Cys Tyr Glu Ala Ile Leu His Arg Gly Asp
160                 165                 170 att atc aca gaa tgt tct tct gct aat gtc tat ggt att aaa gat ggt     996
Ile Ile Thr Glu Cys Ser Ser Ala Asn Val Tyr Gly Ile Lys Asp Gly
175                 180                 185                 190 aaa ctt tat acg cac cca gca aat aac tac atc tta aat ggt att aca    1044
```

-continued

```
                Lys Leu Tyr Thr His Pro Ala Asn Asn Tyr Ile Leu Asn Gly Ile Thr
                                195                 200                 205 cgc caa gtt ata tta aaa tgt gcc gct gaa ata aat tta cca gtg att         1092
Arg Gln Val Ile Leu Lys Cys Ala Ala Glu Ile Asn Leu Pro Val Ile
            210                 215                 220 gaa gag ccg atg aca aaa ggc gat tta tta aca atg gat gaa att att         1140
Glu Glu Pro Met Thr Lys Gly Asp Leu Leu Thr Met Asp Glu Ile Ile
        225                 230                 235 gtg tct tct gtt tca tct gaa gtg aca ccg gtt atc gat gtg gat ggt         1188
Val Ser Ser Val Ser Ser Glu Val Thr Pro Val Ile Asp Val Asp Gly
    240                 245                 250 cag caa att ggt gca ggt gtt cct ggt gaa tgg act cgt aaa ttg caa         1236
Gln Gln Ile Gly Ala Gly Val Pro Gly Glu Trp Thr Arg Lys Leu Gln
255                 260                 265                 270 aaa gca ttt gag gca aaa tta cca att tca att aat gcc taatctgtat         1285
Lys Ala Phe Glu Ala Lys Leu Pro Ile Ser Ile Asn Ala
                275                 280 aaatgattaa aaagagctac ctaaaacttg gttattcgcc aagttaggag ggtagctctt      1345
ttttatagaa caaatatgc atgtattctc ctgaaacgtc atgtaaaata aaaaagatag      1405
cgcctttagt cgatatcac                                                   1424

<210> SEQ ID NO 9
<211> LENGTH: 283
<212> TYPE: PRT
<213> ORGANISM: Bacillus sphaericus

<400> SEQUENCE: 9

Met Ala Tyr Ser Leu Trp Asn Asp Gln Ile Val Glu Glu Gly Ser Ile
 1               5                  10                  15

Thr Ile Ser Pro Glu Asp Arg Gly Tyr Gln Phe Gly Asp Gly Ile Tyr
                20                  25                  30

Glu Val Ile Lys Val Tyr Asn Gly His Met Phe Thr Ala Gln Glu His
            35                  40                  45

Ile Asp Arg Phe Tyr Ala Ser Ala Glu Lys Ile Arg Leu Val Ile Pro
        50                  55                  60

Tyr Thr Lys Asp Val Leu His Lys Leu Leu His Asp Leu Ile Glu Lys
65                  70                  75                  80

Asn Asn Leu Asn Thr Gly His Val Tyr Phe Gln Ile Thr Arg Gly Thr
                85                  90                  95

Thr Ser Arg Asn His Ile Phe Pro Asp Ala Ser Val Pro Ala Val Leu
            100                 105                 110

Thr Gly Asn Val Lys Thr Gly Glu Arg Ser Ile Glu Asn Phe Glu Lys
        115                 120                 125

Gly Val Lys Ala Thr Leu Val Glu Asp Val Arg Trp Leu Arg Cys Asp
    130                 135                 140

Ile Lys Ser Leu Asn Leu Leu Gly Ala Val Leu Ala Lys Gln Glu Ala
145                 150                 155                 160

Ser Glu Lys Gly Cys Tyr Glu Ala Ile Leu His Arg Gly Asp Ile Ile
                165                 170                 175

Thr Glu Cys Ser Ser Ala Asn Val Tyr Gly Ile Lys Asp Gly Lys Leu
            180                 185                 190

Tyr Thr His Pro Ala Asn Asn Tyr Ile Leu Asn Gly Ile Thr Arg Gln
        195                 200                 205

Val Ile Leu Lys Cys Ala Ala Glu Ile Asn Leu Pro Val Ile Glu Glu
    210                 215                 220
```

```
Pro Met Thr Lys Gly Asp Leu Leu Thr Met Asp Glu Ile Ile Val Ser
225                 230                 235                 240

Ser Val Ser Ser Glu Val Thr Pro Val Ile Asp Val Asp Gly Gln Gln
                245                 250                 255

Ile Gly Ala Gly Val Pro Gly Glu Trp Thr Arg Lys Leu Gln Lys Ala
            260                 265                 270

Phe Glu Ala Lys Leu Pro Ile Ser Ile Asn Ala
        275                 280

<210> SEQ ID NO 10
<211> LENGTH: 40
<212> TYPE: DNA
<213> ORGANISM: Artificial Sequence
<220> FEATURE:
<223> OTHER INFORMATION: Description of Artificial Sequence:S243N-S

<400> SEQUENCE: 10
gaaatcattg tgtcgtctgt aaattctgag gttacgccag                             40

<210> SEQ ID NO 11
<211> LENGTH: 40
<212> TYPE: DNA
<213> ORGANISM: Artificial Sequence
<220> FEATURE:
<223> OTHER INFORMATION: Description of Artificial Sequence:S243N-AS

<400> SEQUENCE: 11
ctggcgtaac ctcagaattt acagacgaca caatgatttc                             40

<210> SEQ ID NO 12
<211> LENGTH: 40
<212> TYPE: DNA
<213> ORGANISM: Artificial Sequence
<220> FEATURE:
<223> OTHER INFORMATION: Description of Artificial Sequence:A182S-S

<400> SEQUENCE: 12
gtgacagaat gctcttcatc taatgtttac ggaattaaag                             40

<210> SEQ ID NO 13
<211> LENGTH: 40
<212> TYPE: DNA
<213> ORGANISM: Artificial Sequence
<220> FEATURE:
<223> OTHER INFORMATION: Description of Artificial Sequence:A182S-AS

<400> SEQUENCE: 13
ctttaattcc gtaaacatta gatgaagagc attctgtcac                             40
```

METHOD FOR PRODUCING MONATIN

CROSS-REFERENCE TO RELATED APPLICATIONS

The present application is a continuation of PCT/JP2004/009373, filed on Jun. 25, 2004, which claims priority to JP 2003-183291, filed on Jun. 26, 2003.

TECHNICAL FIELD

The present invention relates to a method for producing monatin by separating monatin from an aqueous solution of monatin which contains impurities. More particularly, the present invention relates to a method for producing monatin, the method being suitably applicable to producing monatin by an enzymatic reaction from 4-(indol-3-ylmethyl)-4-hydroxy-2-oxoglutaric acid (hereinbelow referred to as IHOG) which is a monatin precursor.

BACKGROUND ART

Monatin is a naturally occurring sweet amino acid isolated and extracted from roots of shrubs in South Africa, and has a structure shown below. Monatin has sweetness potency which is dozens to thousands of times stronger than that of sucrose, and is anticipated to be used as a sweetener. In addition to (2S, 4S) isomer of monatin, there are three other optical isomers, i.e., (2S, 4R)-isomer, (2R, 4S)-isomer and (2R, 4R)-isomer. All of the isomers have been confirmed to have sweetness potency which is hundreds of times to thousands of times stronger than that of sucrose.

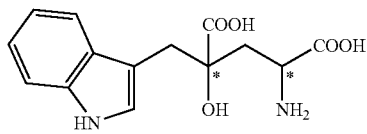

Methods for producing monatin have been reported in the following documents:
(1) U.S. Pat. No. 5,994,559
(2) South Africa Patent No. ZA-874288
(3) Japan Patent No. 2002-60382
(4) Tetrahedron Letters, 42(39):6793-6796, 2001
(5) Organic Letters, 2(19):2967-2970, 2000
(6) Synthetic Communication, 24(22):3197-3211, 1994
(7) Synthetic Communication, 23(18):2511-2526, 1993

DISCLOSURE OF INVENTION

Although there are several reports of methods for producing and separating monatin, usefulness of monatin has been just found and no method for producing monatin at an industrial scale nor method for efficiently separating the resulting monatin has been established yet.

Under such circumstances, the present inventors have developed a novel method for synthesizing monatin including the following reaction steps (1) and (2) using indole-3-pyruvic acid and pyruvic acid, that are easily available on an industrial scale.

(1) A reaction step of synthesizing precursor keto acid (IHOG) by aldol condensation of indole-3-pyruvic acid and pyruvic acid (or oxaloacetic acid)

(2) A reaction step of aminating IHOG at 2-position of IHOG.

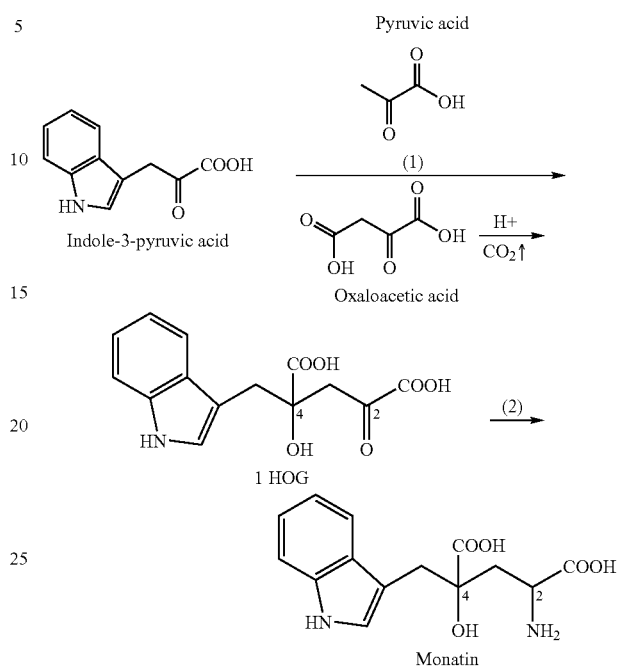

In the aforementioned synthesis of monatin, examples of the enzymes used for catalyzing the amination reaction of (2) may include an aminotransferase which catalyzes an amino group transfer to IHOG, and a dehydrogenase which catalyzes a reductive amination of IHOG.

A reaction solution after performing such an enzyme reaction may contain unreacted IHOG and several byproducts generated from IHOG in addition to monatin. Additionally, such a solution may also contain impurities such as organic components, for example, an enzyme, a coenzyme and an amino group donor that had been used in the reaction. Therefore, efficient removal of these many impurities such as unreacted substrates and byproducts is a major task for obtaining pure monatin from the enzyme reaction solution of monatin produced by the enzymatic method. Such an enzyme reaction solution containing monatin is one typical example of solutions to be treated in the present invention as described later.

As a method for separating monatin, ZA-874288 discloses a purifying method by absorbing natural monatin contained in a plant root into a strong acidic resin, followed by eluting monatin therefrom with an alkali solution such as ammonia.

JP-2002-60382 A Publication also discloses a method for purifying monatin by separating a chemically synthesized stereoisomer monatin mixture with a silica gel modified with an aliphatic alkyl chain such as octadecyl group, and further absorbing monatin into a strongly acidic resin, followed by eluting monatin therefrom with an alkali solution such as ammonia solution.

In ZA-874288, monatin is produced by separating a monatin precursor mixture by silica gel modified with an aliphatic alkyl group such as octadecyl group, followed by alkali hydrolysis, although this method is not the method for directly separating monatin.

However, extraction of the monatin precursor (IHOG) from the enzyme reaction solution upon separating monatin has been difficult in any of the previously reported methods for separating monatin. In terms of production cost, it is preferable to recover unreacted IHOG as well upon separating monatin from the enzyme reaction solution and reuse the recovered IHOG for the production of monatin.

One of the possible reasons why IHOG was unrecoverable by the conventional methods is instability of IHOG in extreme pH. In the prior-art methods for separating monatin, monatin is absorbed into the strongly acidic resin and then eluted therefrom with the alkali solution such as an ammonia solution. Therefore, IHOG is decomposed at the stage of separation, which impedes efficient recover of IHOG (see Reference Example 3).

Therefore, it is desired to develop a method for efficiently separating monatin under a mild pH condition so that IHOG can be recovered without its decomposition simultaneously with the separation of monatin.

A problem to be solved by the present invention is to provide a method for producing monatin in which monatin is efficiently separated on an industrial scale and IHOG, the precursor thereof, is also recoverable.

As a result of conducting an extensive study for solving the aforementioned problems, the present inventors have found out that monatin may be efficiently separated under a mild pH condition by treating an enzyme reaction solution containing monatin with a nonpolar resin having aromatic rings, and completed the present invention based on this finding.

The present inventors have also found that unreacted IHOG left in the enzyme reaction solution may be recovered simultaneously when the enzyme reaction solution is chromatographed on the nonpolar resin having the aromatic rings.

That is, the present invention is as follows:
(1) A method for producing monatin comprising a step of bringing a solution to be treated into contact with a resin to separate monatin from said solution; wherein said solution contains monatin and impurities, and said resin is a nonpolar resin having aromatic rings.
(2) The method for producing monatin according to (1) wherein said nonpolar resin having aromatic rings is a copolymer of styrene and divinylbenzene whose aromatic ring may have one or more substituent selected from the group consisting of halogen atoms and alkyl groups having 1 to 4 carbon atoms.
(3) The method for producing monatin according to (1) or (2) wherein said treating step of said solution is performed at a pH value within the range of 7 to 11.
(4) The method for producing monatin according to any one of (1) to (3) wherein a mixed solvent of water and alcohol is used as an eluent upon treating said solution with said nonpolar resin having aromatic rings.
(5) The method for producing monatin according to any one of (1) to (4) wherein said solution contains a compound as an impurity which is unstable in a pH range lower than pH 7 or higher than 11.
(6) The method for producing monatin according to any one of (1) to (5) wherein said solution contains a product obtained by reacting 4-(indol-3-ylmethyl)-4-hydroxy-2-oxoglutaric acid in the presence of an enzyme which is capable of catalyzing a reaction to generate monatin from 4-(indol-3-ylmethyl)-4-hydroxy-2-oxoglutaric acid.
(7) The method for producing monatin according to (6) wherein said enzyme reaction solution is an enzyme reaction solution obtained by aminating 4-(indol-3-ylmethyl)-4-hydroxy-2-oxoglutaric acid in the presence of aminotransferase and an amino group donor, said aminotransferase being capable of catalyzing a reaction to aminate 4-(indol-3-ylmethyl)-4-hydroxy-2-oxoglutaric acid to generate monatin.
(8) The method for producing monatin according to (7) wherein said amino group donor comprises at least one sort of amino acid selected from alanine, glutamic acid and aspartic acid.
(9) The method for producing monatin according to any one of (6) to (8) wherein 4-(indol-3-ylmethyl)-4-hydroxy-2-oxoglutaric acid contained in said solution is recovered upon treating said solution with said nonpolar resin having aromatic rings.

BEST MODES FOR CARRYING OUT THE INVENTION

Figure 1:
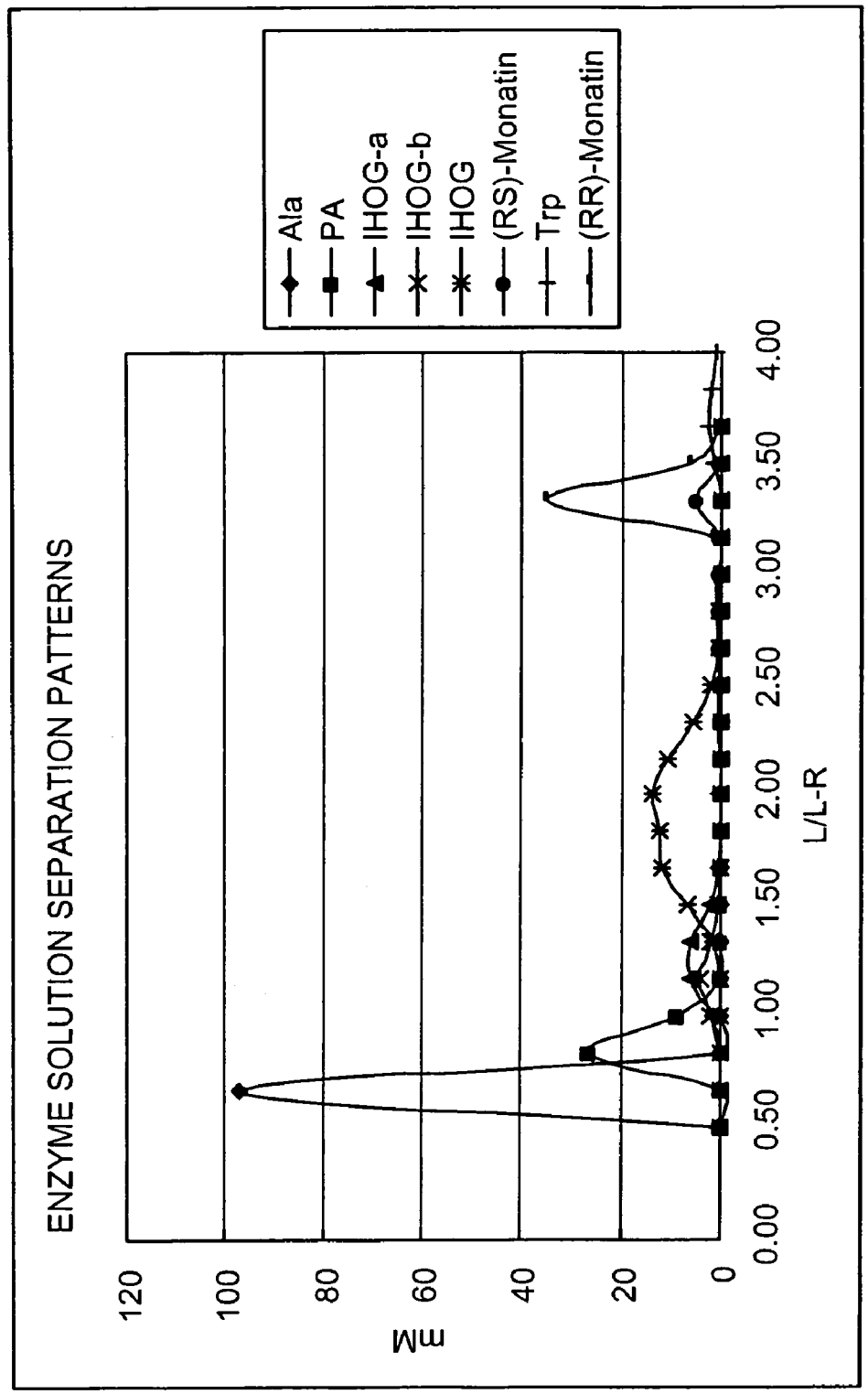
FIG. 1 is a graph showing separation patterns of an enzyme reaction solution.

The method for producing monatin according to the present invention is characterized in that a solution to be treated that contains monatin and impurities is treated a nonpolar resin having aromatic rings, by which monatin in the solution is separated.

When the solution is treated with the nonpolar resin having aromatic rings, each of monatin and the impurities in the solution interacts with the nonpolar resin having aromatic rings. Since the level of the interaction varies depending on each component, the components are liberated from the nonpolar resin in the order of the level of interaction from the weakest to the strongest. For example, when monatin and IHOG are contained in the solution to be treated, first IHOG is eluted and then monatin is eluted. Monatin may be separated from the solution contaminated with the impurities, by taking advantage of this difference of the interaction levels.

As the method for separating monatin, the method of treating with the strongly acidic resin has already been known. However, the present invention is a novel method in which monatin is separated using the nonpolar resin having aromatic rings.

It becomes possible to separate monatin under the mild pH condition by treating the solution with the nonpolar resin having aromatic rings. Therefore, it also becomes possible to recover a compound that is unstable in acid and alkali (e.g., IHOG) simultaneously upon the separation of monatin.

In the conventional method, monatin is absorbed into the strongly acidic resin and then eluted therefrom with the alkali solution such as ammonia solution. IHOG that is unstable in alkali is decomposed through the recovery steps, which makes it difficult to efficiently recover and reuse IHOG in the enzyme reaction solution. In accordance with the present invention; however, monatin is absorbed into the nonpolar resin having aromatic rings, and subsequently monatin may be eluted using an eluate in a pH range at which IHOG can be kept stably. Therefore, the advantage of the present invention is exerted particularly when IHOG is also to be recovered simultaneously with the separation of monatin.

The method for producing monatin of the present invention will be described in detail in the following order.

[A] preparation of a solution to be treated
   (A-1) Preparation of IHOG
   (A-2) Enzyme reaction solution containing monatin

[B] Method for separating monatin
   (B-1) Nonpolar resin having aromatic rings
   (B-2) Handling of the solution to be treated

[A] Preparation of a Solution to be Treated

In the present invention, monatin is separated from "a solution to be treated" that is an aqueous solution in which monatin (including salts thereof) and at least one impurity other than monatin are dissolved. The solution to be treated is the aqueous solution, but may contain another solvent other than water as long as the solvent does not impede the subsequent separation step of monatin.

Monatin in the solution to be treated may be in a salt form other than a free form. What is referred to as monatin in the present invention includes any forms of free monatin and salts thereof unless otherwise indicated. The salt form may include salts with bases. Examples of bases may include inorganic bases such as sodium hydroxide, potassium hydroxide and calcium hydroxide, and ammonia, and organic bases such as various amines.

Examples of such a solution to be treated may include a reaction solution obtained by performing a generation of monatin by an enzymatic reaction method or a chemical synthetic method. The reaction solution may contain impurities such as unreacted raw materials of monatin, reaction byproducts, a reaction catalyst and an enzyme, in addition to monatin generated through the reaction.

In the present invention, it is preferable to use an enzyme reaction solution obtained by reacting IHOG in the presence of an enzyme which catalyzes the reaction to generate monatin from IHOG. Such an enzyme reaction solution contains IHOG remaining unreacted in addition to monatin. IHOG is a compound unstable in extreme pH. However, the method for producing monatin of the present invention enables recovery of IHOG without its decomposition. The recovered IHOG may be reused for the generation of monatin. The method for preparing the enzyme reaction solution will be described below.

(A-1) Preparation of IHOG

IHOG, the monatin precursor, is obtainable by aldol condensation of indole-3-pyruvic acid and pyruvic acid (or oxaloacetic acid).

The method for obtaining IHOG is not particularly limited, and may be either the chemical synthesis method or the enzymatic method. As the method for preparing IHOG, the chemical synthesis method and the enzymatic method will be described separately as follows.

(i) Preparation of IHOG by Chemical Synthesis Method

The preparation of IHOG by the chemical synthesis method may easily be performed using the method described below or the method of Reference Example 2 which will be described later, although not limited thereto.

For example, IHOG may be produced by subjecting indole-3-pyruvic acid and oxaloacetic acid to a cross-aldol reaction and a decarboxylation reaction. A compound which is an important intermediate may be obtained in the reaction system of the aforementioned aldol reaction. This compound may be subjected to the subsequent decarboxylation step without isolation.

There is no particular difficulty in determining the conditions for the aldol reaction. The reaction easily proceeds by simply admixing substituted pyruvic acid and oxaloacetic acid to an appropriate solvent in the presence of the inorganic base or the organic base.

The solvent therefor is not particularly limited as long as the solvent is inert in the reaction.

Those skilled in the art may appropriately select the reaction temperature, the amount of the base to be added, the reaction time period and the operation for adding starting materials in ranges which does not impede practice of the present invention.

Examples of the solvents may preferably include polar solvents such as water, methanol, acetonitrile and dimethylformamide.

Exampled of the base to be used may preferably include inorganic bases such as hydroxide or carbonate of alkali metal or alkali earth metal, e.g., lithium hydroxide, sodium hydroxide, potassium hydroxide, sodium carbonate, potassium carbonate and calcium carbonate, and organic bases such as triethylamine.

The reaction temperature is preferably about −20 to 100° C. and more preferably about 0 to 60° C.

The reaction for decarboxylating the aldol reaction condensate may be accomplished by a spontaneous decarboxylation reaction. However, the decarboxylation reaction may be performed in more effective manner by adding either an acid or metal ions or both to the reaction solution. Examples of the acid therefor may include hydrochloric acid, sulfuric acid, phosphoric acid, acetic acid, para-toluenesulfonic acid, and solid acid such as ion exchange resins, and examples of the metal ions therefor may include transition metal ions such as nickel ions, copper ions and iron ions. The reaction temperature is preferably about −10 to 100° C. and more preferably about 0 to 60° C.

(ii) Preparation of IHOG by Enzymatic Method

Enzymatic preparation of IHOG may be performed with an enzyme which catalyzes the aldol reaction to generate IHOG from indole-3-pyruvic acid and pyruvic acid (or oxaloacetic acid) (the enzyme is hereinbelow referred to as an aldolase).

Such an aldolase has been confirmed to be present in microorganisms belonging to genera *Pseudomonas, Erwinia, Flavobacterium* and *Xanthomonas*. Among them, strains of *Pseudomonas taetrolens* ATCC 4683, *Pseudomonas coronafaciens* AJ 2791, *Pseudomonas desmolytica* AJ 1582, *Erwinia* sp. AJ 2917, *Xanthomonas citri* AJ 2797 and *Flavobacterium rhenanum* AJ 2468 are preferable. Among others, *Pseudomonas taetrolens* ATCC 4683 and *Pseudomonas coronafaciens* AJ 2791 are particularly preferable. Particulars of deposition of these microorganisms are detailed below.

(1) *Pseudomonas coronafaciens* AJ 2791 strain
  (i) Accession number: FERM BP-8246 (transferred from FERM P-18881)
  (ii) Date of deposit: Jun. 10, 2002
  (iii) Address of the depositary authority: International Patent Organism Depositary, National Institute of Advanced Industrial Science and Technology (Central No. 6, 1-1-1 Higashi, Tsukuba-shi, Ibaraki Prefecture, Japan).

(2) *Pseudomonas desmolytica* AJ 1582 strain
  (i) Accession number: FERM BP-8247 (transferred from FERM P-18882)
  (ii) Date of deposit: Jun. 10, 2002
  (iii) Address of the depositary authority: International Patent Organism Depositary, National Institute of Advanced Industrial Science and Technology (Central No. 6, 1-1-1 Higashi, Tsukuba-shi, Ibaraki Prefecture, Japan).

(3) *Erwinia* sp. AJ 2917 strain
  (i) Accession number: FERM BP-8245 (transferred from FERM P-18880)
  (ii) Date of deposit: Jun. 10, 2002
  (iii) Address of the depositary authority: International Patent Organism Depositary, National Institute of Advanced Industrial Science and Technology (Central No. 6, 1-1-1 Higashi, Tsukuba-shi, Ibaraki Prefecture, Japan).

(4) *Flavobacterium rhenanum* AJ 2468 strain
  (i) Accession number: FERM BP-1862
  (ii) Date of deposit: Sep. 30, 1985
  (iii) Address of the depositary authority: International Patent Organism Depositary, National Institute of Advanced Industrial Science and Technology (Central No. 6, 1-1-1 Higashi, Tsukuba-shi, Ibaraki Prefecture, Japan).

(5) *Xanthomonas citri* AJ 2797 strain
  (i) Accession number: FERM BP-8250 (transferred from FERM P-8462).
  (ii) Date of deposit: Sep. 30, 1985
  (iii) Address of the depositary authority: International Patent Organism Depositary, National Institute of Advanced Industrial Science and Technology (Central No. 6, 1-1-1 Higashi, Tsukuba-shi, Ibaraki Prefecture, Japan).

Each of these strains has been accorded the aforementioned accession number under Budapest Treaty on International Recognition of the Deposit of Microorganisms for the Purpose of Patent Procedure. Restrictions on the availability to the public of these strains will be irrevocably removed upon the grant of a patent.

Examples of the aldolase for the generation of IHOG may include an enzyme derived from the microorganism and an enzyme obtained by gene recombination technology.

As to the aldolases derived from *Pseudomonas taetrolens* ATCC 4683 and *Pseudomonas coronafaciens* AJ 2791 (these enzymes will be sometimes abbreviated hereinbelow as "PtALD" and "PcALD", respectively) among the aforementioned microorganisms, the amino acid sequences and DNA sequences thereof have been specified. Thus, it is also preferable to produce the aldolase on a large scale using the gene recombination technology by taking advantage of these DNA sequences.

The DNA sequence encoding PtALD is shown in SEQ ID NO:1. The amino acid sequence of PtALD encoded by the nucleotide sequence in SEQ ID NO:1 is shown in SEQ ID NOS:2 and 3. SEQ ID NO:2 is the amino acid sequence of PtALD encoded by the nucleotide sequence at positions 456 to 1118 in the nucleotide sequence described in SEQ ID NO:1. SEQ ID NO:3 is the amino acid sequence of PtALD encoded by the nucleotide sequence at positions 444 to 1118 in the nucleotide sequence described in SEQ ID NO:1.

The DNA sequence encoding PcALD is shown in SEQ ID NO:4. The amino acid sequence of PcALD encoded by the nucleotide sequence in SEQ ID NO:4 is shown in SEQ ID NO:5. SEQ ID NO:5 is the amino acid sequence encoded by the nucleotide sequence at positions 398 to 1141 in the nucleotide sequence described in SEQ ID NO:4.

To acquire the aldolase, the aldolase may be generated and accumulated by culturing the above aldolase-producing microorganisms. The aldolase may also be generated and accumulated by obtaining transformants which produce the aldolase by the recombinant DNA technology and then culturing the transformants.

To allow the reaction to progress in the presence of the aldolase, the reaction solution which contains the aldolase, indole-3-pyruvic acid, and at least one of oxaloacetic acid and pyruvic acid may be adjusted to an appropriate temperature at 20 to 50° C., kept at pH 6 to 12, and left stand, shaken or stirred for 30 minutes to 5 days.

The reaction rate may be accelerated by adding bivalent cations such as $Mg^{2+}$, $Mn^{2+}$, $Ni^{2+}$ and $Co^{2+}$ to the reaction solution. In terms of cost, $Mg^{2+}$ is preferably used.

When these bivalent cations are added to the reaction solution, any salt may be used as long as the salt does not inhibit the reaction, but preferably $MgCl_2$, $MgSO_4$ or $MnSO_4$ is sometimes used. Although those skilled in the art can determine an addition concentration of these bivalent cations by a simple preliminary study, the concentration thereof may be 0.01 to 10 mM, preferably 0.1 to 5 mM and more preferably 0.5 to 2 mM.

An example of the combination of preferable conditions for the reaction is as follows: washed microbial cells of aldolase-expressing *E. coli* are added as an enzyme source at 10% (w/v) to the reaction solution composed of 100 mM buffer, 50 mM indole-3-pyruvic acid, 250 mM pyruvic acid, 1 mM $MgCl_2$ and 1% (v/v) toluene, and the mixture is then shaken at 33° C. for 4 hours, whereby IHOG is obtained.

(A-2) Enzyme Reaction Solution Containing Monatin

Monatin may be generated by aminating IHOG that has been obtained by the method of (A-1). The amination may be performed as shown in the aforementioned reaction formula. Examples of the enzyme which catalyzes this reaction may include an aminotransferase which catalyzes an amino group transfer reaction to IHOG, and a dehydrogenase which catalyzes a reductive amination reaction of IHOG.

In the present invention, monatin may be generated by allowing such an enzyme or microorganisms having such an objective enzyme activity to act upon IHOG.

The following discussion will be mostly focused on an example in which the aminotransferase is employed as the enzyme.

As the aminotransferase, an enzyme which catalyzes the reaction to generate monatin from IHOG, i.e. the monatin precursor, and an amino group donor is used.

As the amino group donor, a compound comprising an amino group is used. Examples thereof may include amino compounds such as natural and non-natural L-amino acids and D-amino acids. That is, examples of the amino acids may include glutamic acid, aspartic acid, alanine, tryptophan, phenylalanine, isoleucine, leucine, tyrosine, valine, arginine, asparagine, glutamine, methionine, ornithine, serine, cysteine, histidine and lysine. The amino group donor may be used alone or in mixture of two or more.

Alanine, glutamic acid and aspartic acid are preferable as the amino group donor in terms of reactivity. D-Alanine, D-glutamic acid and D-aspartic acid are more preferable. In terms of reactivity and cost, it is particularly preferable to use DL-alanine.

Both L-aminotransferase and D-aminotransferase may be used as the aminotransferase. If L-aminotransferase is used, 2S-monatin is selectively generated by transferring the amino group of the L-amino acid to the 2-position of IHOG. If D-aminotransferase is used, 2R-monatin may be selectively generated by transferring the amino group of the D-amino acid to the 2-position of IHOG.

As variants of monatin which is the subject of the present invention, there are three optical isomers, (2S, 4R)-isomer, (2R, 4S)-isomer and (2R, 4R)-isomer in addition to (2S, 4S)-isomer, and all of them have been confirmed to have the sweetness potency hundreds of times to thousands of times stronger than sucrose. As one preferable aspect in the present invention, it is preferable to generate 2R-monatin which is the isomer having high sweetness, particularly (2R, 4R)-monatin by the use of D-aminotransferase.

When D-amino acid is desired as the amino group donor in this reaction, the D-amino acid donor may be supplied by adding a corresponding L-amino acid into the reaction solution together with an enzyme which catalyzes racemization of the amino acid.

Aminotransferase may be prepared by culturing microorganisms which produce the aminotransferase.

Examples of the microorganisms which produce L-aminotransferase may include microorganisms belonging to genera of *Aeromonas, Agrobacterium, Alcaligenes, Beijerinckia, Escherichia, Proteus* and *Morganella*. Specific examples of these microorganisms may include the followings.

(1) *Aeromonas hydrophila* IFO 3820
(2) *Agrobacterium tumefaciens* IFO. 3058
(3) *Alcaligenes faecalis* ATCC 8750
(4) *Beijerinckia indica* ATCC 9037
(5) *Escherichia coli* ATCC 12814
(6) *Proteus rettgeri* IFO 13501
(7) *Morganella morganii* IFO 3848

Examples of the microorganisms which produce D-aminotransferase may include microorganisms belonging to genera of *Bacillus* and *Paenibacillus*. Specific examples of these microorganisms may include the followings.

(1) *Bacillus sphaericus* ATCC 10208
(2) *Bacillus pulvifaciens* AJ 1327
(3) *Paenibacillus larvae* subsp. *pulvifaciens* ATCC 13537
(4) *Bacillus macerans* AJ 1617
(5) *Paenibacillus macerans* ATCC 8244
(6) *Bacillus lentus* AJ 12699
(7) *Bacillus lentus* ATCC 10840

*Bacillus macerans* AJ 1617 strain has been deposited as follows.

(i) Accession number: FERM BP-8243 (transferred from FERM P-18653 to international deposit on Nov. 22, 2002)
(ii) Date of deposit: Dec. 13, 2001
(iii) Address of the depositary authority: International Patent Organism Depositary, National Institute of Advanced Industrial Science and Technology (Central No. 6, 1-1-1 Higashi, Tsukuba-shi, Ibaraki Prefecture, Japan).

This strain has been accorded the aforementioned accession number under Budapest Treaty on International Recognition of the Deposit of Microorganisms for the Purpose of Patent Procedure. Restriction on the availability to the public of these strains will be irrevocably removed by the grant of a patent.

As to the D-aminotransferases derived from *Bacillus macerans* AJ 1617 and *Bacillus sphaericus* ATCC 10208 (these enzymes will be sometimes abbreviated hereinbelow as "BMDAT" and "BSDAT", respectively) among the above microorganisms, the amino acid sequences and DNA sequences thereof have been specified. Thus, it is also preferable to produce the D-aminotransferase on a large scale using the gene recombination technology by taking advantage of these DNA sequences.

The DNA sequence encoding BMDAT is shown in SEQ ID NO:6. The amino acid sequence of BMDAT encoded by the nucleotide sequence in SEQ ID NO:6 is shown in SEQ ID NO:7.

The DNA sequence encoding BSDAT is shown in SEQ ID NO:8. The amino acid sequence of BSDAT encoded by the nucleotide sequence in SEQ ID NO:8 is shown in SEQ ID NO:9.

In the present invention, it is preferable to efficiently generate monatin product which abundantly contains (2R, 4R)-monatin, i.e. the isomer having the highest sweetness among four optical isomers of monatin. It is also preferable to artificially mutate the D-aminotransferase by substituting an amino acid residue(s) in a part thereof so that (2R, 4R)-monatin is efficiently generated from IHOG.

As a result of the study by the present inventors, it has been found out that modification of BMDAT by introducing a substituent at least at one site of the amino acid residues at positions 100, 180 to 183, 243 and 244 in SEQ ID NO:7 may result in efficient generation of (2R, 4R)-monatin. It has also been confirmed that introduction of a substituent at least at one site of the amino acid residues at positions 243 and 244 of BSDAT in SEQ ID NO:9 may result in efficient generation of (2R, 4R)-monatin.

Monatin may be generated by reacting IHOG and the amino group donor in the presence of the enzyme which catalyzes the reaction to aminate the 2-position of IHOG to generate monatin or the microorganism having the enzyme activity. Reaction efficiency may be enhanced by adding to the reaction system a reaction accelerating substance such as coenzymes, surfactants and organic solvents.

The reaction temperature may usually be in the range in which the enzyme to be used can keep its activity, i.e., preferably 10 to 50° C., more preferably 20 to 40° C. and still more preferably 25 to 37° C. A pH value of the enzyme reaction solution may be adjusted in the range of usually 2 to 12, preferably 7 to 11 and more preferably 8 to 9. Under too higher pH condition, IHOG, i.e. the raw material of monatin, tends to be decomposed spontaneously into indole-3-pyruvic acid and pyruvic acid; whereas, under too lower pH condition, IHOG may be easily cyclized and which impedes amination, none of these conditions being preferable. In order to effectively inhibit the decomposition and the cyclization of IHOG, the raw material of monatin, it is preferable to keep pH at 7 to 11 and more preferably 8 to 9. The reaction time period may be usually about 1 to 120 hours, preferably about 1 to 72 hours and more preferably about 1 to 24 hours.

Quantification of monatin and IHOG in the enzyme reaction solution may be rapidly performed using well-known methods. As a simple method, thin layer chromatography may be used with "Silica gel 60F254" supplied from Merck & Co., Inc. For more precise analysis, high performance liquid chromatography (HPLC) using a reverse phase column such as "Inertsil ODS-80A" supplied from GL Sciences Inc., and "Capsule Pack MG" supplied from Shiseido Co., Ltd., or an optical resolution column such as "CROWNPAK CR(+)" supplied from Daicel Chemical Industries, Ltd. may be used.

After the completion of the enzymatic reaction, the enzyme reaction solution sometimes contains insoluble components such as microbial cells and disrupted microbial cells used as the enzyme source in addition to soluble components such as monatin, IHOG and the amino group donor. In the present invention, it is preferable to previously remove the insoluble components contained in the enzyme reaction solution prior to treating with the nonpolar resin having aromatic rings. The insoluble components may be removed by ordinary techniques such as centrifugation and filtration.

[B] Method for Separating Monatin

In the present invention, monatin is separated from the solution to be treated containing monatin and impurities, by treating the solution with the nonpolar resin having aromatic rings.

As used herein, "treating the solution to be treated with the nonpolar resin having aromatic rings" means that the solution is passed through the nonpolar resin having aromatic rings so that the solution contacts with its surface.

The nonpolar resin having aromatic rings has no functional group such as ion-exchange group, but absorbs an organic component by van der Waals force. When the solution is treated with the nonpolar resin having aromatic rings, monatin and the impurities interact with the nonpolar resin having aromatic rings and are absorbed into the surface of the nonpolar resin. Since the level of the interaction varies depending on each component, when an eluate is run on the surface of the nonpolar resin, the components are liberated from the nonpolar resin in the order of the level of interaction from the weakest to the strongest. Monatin may be separated and isolated from the solution which contains the impurities, by taking advantage of this difference of the interaction.

(B-1) Nonpolar Resin Having Aromatic Rings

In the present invention, the solution to be treated is treated with the nonpolar resin having aromatic rings in the molecule. It is preferable that such a nonpolar resin has the aromatic rings in a side chain. The nonpolar resin preferably has the aromatic rings at high density in the molecule. Specifically, it is preferable that 20% or more and preferably 50% or more carbon atoms contained in the molecule of the nonpolar resin are derived from the aromatic rings.

Examples of the aromatic rings contained in the molecule of the nonpolar resin may include benzene rings, naphthalene rings and anthracene rings. Among them, the benzene ring is the most preferable. The aromatic rings contained in the molecule of the nonpolar resin may have substituents as long as the substituent does not affect the efficiency for separating monatin, and specifically may have the substituents such as halogen atoms and alkyl groups having 4 or less carbon atoms. Among them, the preferable substituent may include the halogen atom, and among others, bromine is particularly preferable.

When the halogen atom is introduced into the aromatic rings contained in the molecule of the nonpolar resin, hydrophobic absorbability is enhanced. Thus, when the organic components are eluted from the nonpolar resin, a larger amount of the eluate is required. Therefore, the difference in elution time of each component is increased, resulting in obtaining monatin fraction having high purity and containing less impurities.

The nonpolar resin having aromatic rings particularly suitably used in the present invention may be a polymer having a three dimensional crosslinking structure obtained by polymerizing styrene and divinylbenzene. Styrene and divinylbenzene therefor may have substituents such as halogen atoms in their benzene rings. The nonpolar resin having aromatic rings may partially includes a unit derived from a monomer having no aromatic ring (e.g., ethylene) as long as the nonpolar resin is the polymer whose major structure is a unit derivatized from styrene and divinylbenzene.

The preferable mode for carrying out the invention may be a treatment using a so-called chromatographic technique in which a column is filled with the nonpolar resin having aromatic rings in a particulate form and the solution to be treated is passed through this column.

An average particle diameter of particles made of the nonpolar resin having aromatic rings is preferably 0.1 to 1 mm and more preferably 0.2 to 0.4 mm in a swelling state. The average particle diameter referred to herein is obtained by an effective diameter calculation method. The effective diameter calculation method is the method of calculating diameter size of sieve openings through which 90 vt % particles pass when the particles are applied to the sieve (effective diameter). Specifically, the particles are applied to multiple sieves whose opening diameters are different, a volume of the remaining particles is obtained for each sieve, and a cumulative total (%) of the remaining volume is put on one axis and a diameter (mm) is put on another axis to plot on logarithmic probability sheet. Three points are taken sequentially from a larger amount of the remaining particles, and a line is drawn so as to satisfy these three points as possible. The diameter (mm) of the sieve opening, which corresponds to 90% cumulative total of the remainings is obtained from this line, and is referred to as the effective diameter.

The particle size distribution of the particles is not particularly limited, but may preferably be 2.0 or less in terms of a value calculated by a uniformity coefficient calculation method. The uniformity coefficient is calculated in accordance with the following: the diameter (mm) of the sieve opening which corresponds to 40% cumulative total of the remaining is calculated in the same way as in the effective diameter calculation method, and the uniformity coefficient is then calculated by the following formula:

$$\text{Uniformity coefficient} = \text{Diameter (mm) of the sieve opening which corresponds to 40\% cumulative total of the remaining}/\text{Effective diameter (mm)}$$

The specific surface area of the particles made of the nonpolar resin having aromatic rings is preferably 200 to 2000 $cm^2/g$ and more preferably 500 to 1500 $cm^2/g$.

The particles made up of the nonpolar resin having aromatic rings are preferably porous particles having many fine pores. The pore radius of the porous particle is 10 to 500 angstroms, preferably 30 to 300 angstroms and more preferably 50 to 150 angstroms. The pore volume of the porous particle is preferably 1 mL or more per g of the resin.

(B-2) Handling of Solution to be Treated

The treatment temperature of the solution to be treated is 0 to 80° C. and more preferably 10 to 50° C. When the treatment is performed in a too low temperature, crystals may be precipitated from the solution to reduce a yield. When the treatment is performed in a too high temperature, the decomposition and coloration occur to reduce the quality of monatin.

When the solution to be treated is contacted with the surface of the nonpolar resin having aromatic rings, each of monatin and the impurities interacts with the nonpolar resin having aromatic rings and is absorbed into the surface of the nonpolar resin. Since the level of the interaction varies depending on each component, the components are liberated from the nonpolar resin in the order of the level of interaction from the weakest to the strongest. Monatin may be separated from the solution which contains the impurities by taking advantage of this difference of the interaction.

In the present invention, it is preferable to bring the solution to be treated into contact with the surface of the nonpolar resin having aromatic rings, and subsequently elute/develop each component using the eluate.

The solvent used as the eluate may be any organic solvent which is miscible with water. Alcohol solvents such as methanol, ethanol and propanol are preferable as the organic solvent. The mixture ratio of the solvent to water is preferably 0.1 to 100%, more preferably 1 to 50% and still more preferably 5 to 25%. When eluted with water itself, it takes long time to elute monatin. Thus, it is also possible to once elute water-soluble impurities with water and then elute monatin with the mixture of the organic solvent and water. When alcohol is contained too abundantly, separability from the other components is reduced.

The value of pH in the solution to be treated may be 2 to 12, more preferably 7 to 11 and particularly preferably 8 to 9. In a strongly acidic region, monatin is partially decomposed into lactam and lactone.

When the solution to be treated is strongly acidic or alkaline and contains IHOG, IHOG is decomposed and can not be recovered. Specifically, IHOG is easily cyclized in the strongly acidic solution. This cyclization is an irreversible reaction, and therefore, it is difficult to regenerate the cyclized IHOG to reuse for the monatin production. In the strongly alkaline solution, IHOG which is the raw material of monatin is easily decomposed into indole-3-pyruvic acid and pyruvic acid spontaneously, which is not preferable. In order to effectively inhibit the decomposition and the cyclization of IHOG, it is preferable to keep the solution to be treated preferably at pH 7 to 11 and more preferably pH 8 to 9.

The use amount of the nonpolar resin having aromatic rings is preferably 20 to 200 L/mol and more preferably 50 to 100 L/mol based on the amount of monatin contained in the solution to be treated. When the amount to be used is too small, the separability of monatin from the other components is reduced whereas when it is too large, the amount of eluate used is increased, which is not economical.

An empirical value of an elution volume (eluate volume/resin volume [L/L-R]) at which monatin is eluted may be confirmed by sampling the eluate every predetermined period of time and measuring elution behavior of each component using HPLC. The elution volume varies depending on a treatment condition. When the solution to be treated contains monatin and IHOG, first IHOG is eluted and then monatin is eluted. Each of IHOG fraction and a monatin fraction may be collected by previously figuring out the elution volume at which IHOG has been eluted and the elution volume at which monatin has been eluted.

EXAMPLES

The present invention will be more specifically with reference to the following Examples, but the invention is not limited to these Examples.

In the present Examples, monatin was quantified by high performance liquid chromatography using "Inertsil ODS-80A" (5 μm, 6×150 mm) supplied from GL Sciences Inc., or "Capsule Pack MG" (5 μm, 6×250 mm) supplied from Shiseido Co., Ltd. Analytical conditions are as follows.

With "Inertsil ODS-80A" (5 μm, 6×150 mm) supplied from GL Sciences Inc.:
Mobile phase: aqueous solution of 12% (v/v) acetonitrile/0.05% (v/v) trifluoroacetic acid
Flow rate: 1.5 mL/minute
Column temperature: 30° C.
Detection: UV 210 nm
Under these analytical conditions, monatin isomers can be quantified in a separate manner with a retention time of 12.1 minutes for (2S, 4S)-monatin and (2R, 4R)-monatin, and with a retention time of 9.7 minutes for (2S, 4R)-monatin and (2R, 4S)-monatin.

With "Capsule Pack MG" (5 μm, 4.6×250 mm) supplied from Shiseido Co., Ltd.:
Mobile phase solution A: aqueous solution (20 mM monopotassium phosphate+20 mM dipotassium phosphate)
Mobile phase solution B: aqueous solution (20 mM monopotassium phosphate+20 mM dipotassium phosphate)/acetonitrile (50/50, v/v)
Time program: 0 to 15 minutes, 100% solution A; 15 to 45 minutes, linear gradient up to 75% solution B; 45 to 60 minutes, 100% solution A
Analytical cycle: 60 minutes
Flow rate: 1 mL/minute
Column temperature: 40° C.
Detection: UV 210 nm
Under these analytical conditions, monatin isomers can be quantified in a separate manner with a retention time of 16.3 minutes for (2S, 4S)-monatin and (2R, 4R)-monatin, with a retention time of 12 minutes for (2S, 4R)-monatin and (2R, 4S)-monatin, and with a retention time of 11 minutes for IHOG.

If necessary, an additional analysis by high performance liquid chromatography using an optical resolution column such as "CROWNPAK CR(+)" (4.6×150 mm) supplied from Daicel Chemical Industries, Ltd. was also performed. The analytical conditions are as follows.

Mobile phase: aqueous solution of perchloric acid (pH 1.5)/10% (v/v) methanol
Flow rate: 0.5 mL/minute
Column temperature: 30° C.
Detection: UV 210 nm
Under these analytical conditions, the monatin optical isomers can be separately quantified in order of (2R, 4S), (2R, 4R), (2S,4R) and (2S, 4S) with retention times of 42, 57, 64 and 125 minutes, respectively.

Example 1

121.84 g of an enzyme reaction solution (containing 2.72 wt % of (2R, 4R)-monatin (sometimes represented as (RR) monatin)) obtained by generating monatin from IHOG in accordance with Reference Example 1 was passed through a resin column (diameter: 4 cm) filled with 600 mL of a synthetic absorbent (DIAION-SP 207 supplied from Mitsubishi Chemical Corporation). Purified water was then passed through the column at a flow rate of 7.5 mL/minute for 3 hours. An aqueous solution of 15% 2-propanol was then passed through the column at a flow rate of 7.5 mL/minute for 3 hours and fractions of 2.6 to 3.5 (eluate volume/resin volume [L/L-R]) was collected, whereby monatin was almost quantitatively fractionated.

Separation patterns of the enzyme reaction solution are shown in FIG. 1. In FIG. 1, PA represents pyruvic acid generated through the decomposition of IHOG and the amino group transfer reaction of D-alanine. IHOG-a represents 1,3-dihydroxy-2,3,4,9-tetrahydro-1H-carbazole-1,3-dicarboxylic acid (see the following chemical formula) produced by cyclization of IHOG. IHOG-b represents 2-hydroxy-3-(1H-indol-3-yl)-2-methyl-4-oxo-pentanedioic acid (see the following chemical formula) produced as a byproduct when IHOG was synthesized by aldol condensation of indole-3-pyruvic acid and pyruvic acid.

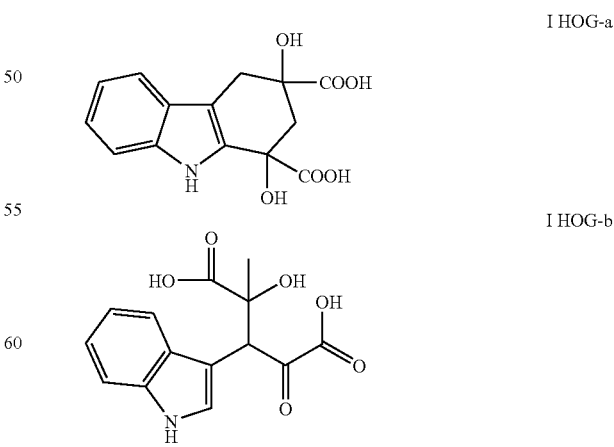

The resulting monatin fraction was concentrated down to 13.3 g, and 64 mL of 2-propanol was added, which was then stirred at 10° C. for 16 hours. After filtrating crystals, 3.0 g of the resulting wet crystals were dissolved in 10 mL of water. 30 mL of 2-propanol was added thereto at 35° C., and 30 mL of 2-propanol was further dropped over 2 hours at 35° C. The solution was cooled to room temperature, and the crystals were filtrated and subsequently dried under reduced pressure to yield 2.59 g of a K salt of (2R, 4R)-monatin (area purity: 97.4%).

Examples 2 to 9, Comparative Example 1

An enzyme reaction model solution (2 mL) was injected in a resin column (diameter: 4 cm) filled with 40 mL of a synthetic absorbent (supplied from Mitsubishi Chemical Corporation) shown in Table 1. In the enzyme reaction model solution, 0.24 mmol monatin, 1 mmol alanine, 0.24 mmol IHOG and 0.17 mmol IPA (indole pyruvic acid) were contained. An eluate in the mobile phase described in Table 1 was passed through the column, and the eluate was sampled every predetermined time to measure the elution behavior of each component by HPLC.

The average elution volume (L/L-R) of each component was shown in Table 1. The average elution volume (L/L-R) herein is a value calculated by a weighted average method.

The chemical structures and properties of the synthetic absorbents in Table 1 are shown in Table 2. The apparent density, the water content, the effective diameter and the uniformity coefficient described in Table 2 are values calculated in accordance with the following:

Apparent density=Resin Weight (wet, g)/Resin volume (L-R)

The resin volume is the value measured in a standard form (swelling state), and the resin weight is the value measured after the resin in the standard form is centrifuged to remove adhering water.

Water content (%)=Loss weight after drying (g)×100/ Resin weight (wet, g)

The resin weight is the value measured after the resin in the standard form is centrifuged to remove adhering water. The loss weight after drying is the value measured after the resin after measuring the resin weight was dried in a constant temperature dryer at 105±2° C. for 4 hours followed by being cooled in a desiccator for 30 minutes.

Effective diameter: particle size of the resin calculated by the effective diameter calculation method Uniformity coefficient: particle size distribution of the resin calculated by the uniformity coefficient calculation method.

TABLE 1

| EXAMPLE | RESIN | MOBILE PHASE | AVERAGE ELUTION VOLUME (L/L-R) | | | |
|---|---|---|---|---|---|---|
| | | | MONATIN | ALANINE | IHOG | IPA |
| 2 | SP207 | H20 | 5.20 | 0.95 | 2.11 | 7.28 |
| 3 | SP207 | 1% i-ProOH | 2.07 | 0.73 | 1.08 | 2.99 |
| 4 | SP207 | 5% i-ProOH | 1.18 | 0.66 | 0.76 | 1.57 |
| 5 | SP207 | 10% i-ProOH | 0.84 | 0.60 | 0.74 | 1.09 |
| 6 | SP825 | H20 | 3.38 | 0.65 | 1.10 | 8.83 |
| 7 | SP850 | H20 | 4.61 | 0.69 | 1.58 | 12.44 |
| 8 | HP21 | H20 | 2.14 | 0.86 | 1.25 | 2.81 |
| 9 | HP20 | H20 | 1.68 | 0.71 | 1.01 | 2.72 |
| COMPARATIVE EXAMPLE 1 | HP2MG | H20 | 0.96 | 0.74 | 0.80 | 1.56 |

IPA; Indole pyruvic acid
IHOG; 4-(Indol-3-ylmethyl)-4-hydroxy-2-oxoglutaric acid

TABLE 2

| BRAND | DIAION HP20 | DIAION HP21 | SEPABEADS SP825 | SEPABEADS SP850 | SEPABEADS SP207 | DIAION HP2MG |
|---|---|---|---|---|---|---|
| CHEMICAL STRUCTURE | | —CH₂—CH—CH₂CH— (diphenyl structure) —CH₂CH— | | | —CH₂—CH—CH₂CH— (diphenyl structure with Br) —CH₂CH— Br | CH₃ and CH₃ groups with —CH₂—C—CH₂—C— backbone, CO, COOCH₃, O, (CH₂)₂, O, CO, —CH₂—C—, CH₃ |
| APPARENT DENSITY (REFERENCE VALUE) g/L-R | 680 | 625 | 690 | 670 | 780 | 720 |

TABLE 2-continued

| BRAND | DIAION HP20 | DIAION HP21 | SEPABEADS SP825 | SEPABEADS SP850 | SEPABEADS SP207 | DIAION HP2MG |
|---|---|---|---|---|---|---|
| WATER % | 55 TO 65 | 45 TO 55 | 52 TO 62 | 46 TO 52 | 43 TO 53 | 55 TO 65 |
| PARTICLE SIZE DISTRIBUTION >250 μm | | | | 90% OR MORE | | 95% OR MORE |
| EFFECTIVE DIAMETER mm | | | | 0.25 OR MORE | | 0.35 OR MORE |
| UNIFORMITY COEFFICIENT | | | | 1.6 OR LESS | | 1.6 OR LESS |
| FINE PORE DISTRIBUTION mL/g | 1.3 | 1.1 | 1.4 | 1.2 | 1.3 | 1.2 |
| SPECIFIC SURFACE AREA m2/g | 600 | 570 | 1000 | 1000 | 600 | 500 |
| FINE PORE RADIUS Å | >200 | 80-120 | 50-60 | 35-45 | 80-120 | 200-300 |

Comparative Example 2

An aqueous solution (10 mL) containing 300 mg of monatin and 484 mg of alanine was applied onto 50 mL of strongly acidic resin (DIAION-PK208 Na type supplied from Mitsubishi Chemical Corporation). Purified water was passed therethrough at a flow rate of 1 mL/minute. Monatin was eluted without separating from alanine.

Comparative Example 3

An aqueous solution (10 mL) containing 250 mg of monatin and 534 mg of alanine was applied onto 25 mL of alkaline resin (DIAION-WA30 supplied from Mitsubishi Chemical Corporation). Purified water was passed therethrough at a flow rate of 1 mL/minute. Alanine was separated and eluted. However, monatin was not eluted but kept absorbed in the resin.

Reference Example 1

Preparation of Enzyme Reaction Solution

[I] Cloning of dat gene derived from Bacillus macerans AJ 1617 strain (bmdat) and collection of expression plasmid (1) Preparation of Chromosomal DNA Bacillus macerans AJ 1617 strain were cultured in 50 mL of a broth medium at 30° C. overnight (pre-cultivation) This culture medium (5 mL) was inoculated into 50 mL of the broth medium to conduct a main cultivation. After culturing up to a logarithmic growth late phase, 50 mL of the cultured medium was subjected to centrifugation (12,000×g, 4° C., 15 minutes) to collect the microorganisms. A chromosomal DNA was prepared using these microbial cells in accordance with standard methods.

(2) Isolation of bmdat Gene from Gene Library

30 μg of the chromosomal DNA of Bacillus macerans AJ 1617 strain was partially digested with 1 U of a restriction enzyme, EcoRI at 37° C. for 3 hours. Fragments of 3 to 6 kbp were collected from this DNA by agarose gel electrophoresis. This was ligated to 1 μg of pUC118 (treated with BAP, supplied from Takara Shuzo Co., Ltd.) that had been cleaved with EcoRI, with which E. coli JM109 was transformed to make a gene library. This was plated on an LB medium (1% tryptone, 0.5% yeast extract, 1% sodium chloride, 2% agar, pH 7.0) containing 0.1 mg/mL of ampicillin to form colonies. A colony thus appeared was inoculated into 1 mL of LB liquid medium containing 0.1 mg/mL of ampicillin and 0.1 mM isobutyl-1-thio-β-D-galactopyranoside (IPTG), and cultured at 37° C. overnight. Microorganisms were collected by centrifuging 200 to 400 μL of the culture medium, and then washed, to yield microbial cells. The collected microbial cells were inoculated into 200 μL of a reaction solution composed of 100 mM Tris-HCl (pH 8.0), 50 mM sodium pyruvate, 100 mM D-glutamic acid, 1 mM pyridoxal-5'-phosphate and 1% toluene (v/v), and reacted at 30° C. for 30 minutes.

After completion of the reaction, 5 μL of a supernatant obtained by centrifugation of the reaction solution was applied to each well of a 96-well plate filled with 200 μL of a reaction solution for pyruvic acid quantification (100 mM Tris-HCl (pH 7.6), 1.5 mM NADH, 5 mM MgCl$_2$, 16 U/mL of lactate dehydrogenase supplied from Oriental Yeast Co., Ltd.). After reacting at 30° C. for 10 minutes, absorbance at 340 nm was measured using a plate reader (SPECTRA MAX190 supplied from Molecular Device). The same reaction was performed by applying sodium pyruvate at a final concentration of 0.2 mM to 1 mM. Using this as a standard, a loss amount of pyruvic acid was quantified to detect a D-aminotransferase (DAT) activity.

A clone which exhibited the DAT activity was collected by the screening of the DAT activity as described above. A plasmid containing D-aminotransferase gene was prepared from this transformant and designated as pUCBMDAT. The plasmid pUCBMDAT was treated with EcoRI and then subjected to the agarose gel electrophoresis, and a length of the inserted fragment was estimated to be about 3.3 kbp.

(3) Nucleotide Sequence of Inserted Fragment

A nucleotide sequence of the inserted fragment in the plasmid pUCBMDAT was determined by a dideoxy method. Consequently, an ORF composed of about 850 bp which corresponds to positions 630 to 1481 in the sequence shown in SEQ ID NO:6 was found out. Homology of this ORF to known sequences was searched. As a result, this ORF exhibited 91% homology to D-aminotransferase gene derived from Bacillus sphaericus ATCC 10208 strain in terms of amino acid sequence, 66% homology to D-aminotransferase gene derived from Bacillus sp. YM-1 strain in terms of amino acid sequence, and 42% homology to D-aminotransferase gene derived from Bacillus licheniformis ATCC 10716 strain in terms of amino acid sequence. These homology values were calculated using gene analysis software "genetyx 6" (supplied from GENETYX) with default parameters. These results demonstrated that this ORF encodes D-aminotransferase gene.

[II] Preparation of Mutant BMDAT-expressing Plasmid

Site-directed mutagenesis for preparing a mutant BMDAT-expressing plasmid was performed with QuickChange Site-Directed Mutagenesis Kit supplied from Stratagene. Synthetic oligo DNA primers (pairs; each consisting of two sequences) designed to introduce objective nucleotide substitutions and to be complementary to each chain of double strand DNA were synthesized. Prepared mutant enzymes and sequences of the synthetic oligo DNA primers used are shown in Table 3. The name of each mutant enzyme represents "an amino acid residue in the wild type enzyme—a residue number—a substituted amino acid residue" in this order. For example, S243N refers to the mutant enzyme obtained by replacing Ser (S) residue at position 243 of the wild type enzyme with Asn (N).

TABLE 3

```
pS243N  S243N-S   GAA ATC ATT GTG TCG TCT GTA AAT TCT GAG GTT ACG CCA G  (40mer,SEQ ID NO:10)
        S243N-AS  CTG GCG TAA CCT CAG AAT TTA CAG ACG ACA CAA TGA TTT C  (40mer,SEQ ID NO:11)

pA182S  A182S-S   GTG ACA GAA TGC TCT TCA TCT AAT GTT TAC GGA ATT AAA G  (40mer,SEQ ID NO:12)
        A182S-AS  CTT TAA TTC CGT AAA CAT TAG ATG AAG AGC ATT CTG TCA C  (40mer,SEQ ID NO:13)
```

In accordance with the instructions of the kit, the mutant plasmid pS243N/A182S was prepared with the wild type BMDAT-expressing plasmid pUCBMDAT obtained in [I] as a template. The method for preparing the plasmid pS243N/A182S will be described. pS243N was prepared by amplifying a mutant BMDAT-expressing plasmid using the primers S243N-S and S243N-AS with pUCBMDAT as a template. Condition for amplification is as follows:

95° C. for 30 seconds
55° C. for one minute and
68° C. for 8 minutes×18 cycles

The template pUCBMDAT was cleaved by treating with a restriction enzyme DpnI which recognizes methylated DNA upon cleavage. Subsequently, E coli JM109 was transformed with the resulting reaction solution. The plasmid was collected from the transformant and sequenced to confirm that the objective nucleotide sequence had been introduced.

Then, the same operation was performed with pS243N as a template and A182S—S and A182S-AS as primers, to obtain pS243N/A182S.

[III] Conversion of (±) IHOG into 2R-Monatin Using S243N/A182S Mutant BMDAT (1) Preparation of Microbial Cells E. coli transformants carrying pS243N/A182S were inoculated into 3 mL of LB medium (1 g/dL bactopeptone, 0.5 g/dL yeast extract, and 1 g/dL NaCl) containing 0.1 mg/mL of ampicillin and pre-cultured at 37° C. for 16 hours. Subsequently, 2.5 mL of this cultured medium was added to 50 mL of casamino acid medium (0.5 g/dL ammonium sulfate, 0.14 g/dL $KH_2PO_4$, 0.23 g/dL disodium citrate.$3H_2O$, 0.1 g/dL $MgSO_4.7H_2O$, 2 mg/dL $FeSO_4$, 2 mg/dL $MnSO_4$, 2 mg/dL pyridoxine hydrochloride, 0.1 mg/dL thiamine, 1 g/dL casamino acid, 0.3 g/dL glycerol, pH 7.5) containing 0.1 mg/mL ampicillin and 0.1 mM IPTG in a 500 mL Sakaguchi flask, and cultured with shaking at 37° C. for 18 hours. Microorganisms were collected from the resulting cultured medium and washed, to prepare S243N/A182S mutant BMDAT-expressing E. coli.

(2) IHOG Amination Reaction

Microbial cells collected from 240 mL of the culture medium and washed in the aforementioned (1) were suspended in 120 mL of a reaction solution composed of 100 mM potassium phosphate buffer (pH 8.3), 244 mM (±)-IHOG, 600 mM DL-Ala and 1 mM pyridoxal-5'-phosphate, and stirred at 37° C. for 24 hours to perform the reaction. (±)-IHOG used in this procedure was obtained by the method in Reference Example 2 which will be described later.

In order to prevent pH from lowering during the reaction, pH was controlled to pH 8.4±0.1 with 1 N KOH. As a result, 79.2 mM of (2R, 4R)-monatin was accumulated in the reaction solution after 24 hours of reaction (molar yield with respect to 4R-IHOG: 65%). The resulting reaction solution was centrifuged at 5,000 rpm for 10 minutes to obtain a supernatant. This supernatant was used as the enzyme reaction solution in Example 1.

Reference Example 2

Synthesis of IHOG 7.50 g of indole-3-pyruvic acid (35.8 mmol, content: 97.0% by weight) and 14.18 g (107.4 mmol) of oxaloacetic acid were dissolved in 64.45 mL of water in which 18.91 g (286.5 mmol, content: 85% by weight) had been dissolved. This mixed solution was stirred at 35° C. for 24 hours.

Further, 40.0 mL of 3N hydrochloric acid was added thereto for neutralization (pH=7.0), to yield 153.5 g of a reaction neutralization solution. In this reaction neutralization solution, 5.55 g of IHOG was contained and the yield was 53.3% (with respect to indole-3-pyruvic acid).

Water was added to this reaction neutralization solution to make the volume thereof 168 mL, which was then passed through a resin column (diameter: 4.8 cm) filled with 840 mL of the synthetic absorbent (DIAION-SP207 supplied from Mitsubishi Chemical Corporation). Further, the purified water was passed therethrough at a flow rate of 23.5 mL/minute and 1.73 to 2.55 (L/L-R) fractions were collected to afford an aqueous solution containing 3.04 g of IHOG at high purity with a yield of 54.7% (with respect to the amount applied onto the resin).

(NMR Measurement)

$^1$H-NMR (400 MHz, $D_2O$): 3.03 (d, 1H, J=14.6 Hz), 3.11 (d, 1H, J=14.6 Hz), 3.21 (d, 1H, J=18.1 Hz), 3.40 (d, 1H, J=18.1 Hz), 7.06-7.15 (m, 3H), 7.39 (d, 1H, J=7.8 Hz), 7.66 (d, 1H, J=7.8 Hz). $^{13}$C-NMR (100 MHz, $D_2O$): 35.43, 47.91, 77.28, 109.49, 112.05, 119.44, 119.67, 121.91, 125.42, 128.41, 136.21, 169.78, 181.43, 203.58.

Reference Example 3

Evaluation of pH stability of IHOG

[I] pH Stability of IHOG in Amination Reaction Solution

In order to examine the stability of IHOG in the IHOG amination solution, change of IHOG amounts with time in an IHOG amination solution was measured without adding the microbial cells. A test tube containing 1 mL of the reaction solution composed of 100 mM potassium phosphate buffer (pH 8.3), 300 mM (±)-IHOG, 600 mM DL-Ala and 1 mM pyridoxal-5'-phosphate was shaken at 37° C. for 40 hours, to perform the reaction. As a result, survival rates of IHOG were reduced to 81% after 16 hours, 70% after 24 hours and 57% after 40 hours, indicating that IHOG was decomposed with time. This is presumed to be attributed to the decomposition of IHOG into indole-3-pyruvic acid and pyruvic acid and the cyclization of IHOG.

[II] pH Stability of IHOG in Buffer

The survival rate of IHOG (0.54 mM) was measured in 40 mM potassium phosphate buffer at different pH. The storage temperature was adjusted to 35° C.

TABLE 4

| pH | Survival rate of IHOG | | | |
|----|------|------|------|------|
|    | 2 hr | 7 hr | 24 hr | 48 hr |
| 7  | 97.4% | 90.0% | 68.4% | 45.6% |
| 8  | 100.6% | 100.1% | 96.4% | 89.6% |
| 9  | 100.6% | 101.1% | 99.0% | 94.4% |
| 10 | 97.0% | 96.8% | 94.2% | 90.8% |
| 11 | 95.6% | 90.7% | 74.8% | 59.3% |

INDUSTRIAL APPLICABILITY

In accordance with the present invention, (2R, 4R)-monatin which has the highest sweetness potency among monatin isomers anticipated as sweeteners may be efficiently produced using the enzymatic reaction. Therefore, the present invention is very useful in the industrial fields, particularly in the field of food industry.

The invention claimed is:

1. A method for isolating monatin and 4-(indol-3-ylmethyl)-4-hydroxy-2-oxoglutaric acid (IHOG) from a solution comprising monatin, IHOG and impurities, wherein the method comprises treating the solution with a resin at a pH within the range of 7 to 11 to separate monatin and IHOG from the solution;

wherein the resin is a nonpolar resin having aromatic rings.

2. The method of claim 1, wherein the nonpolar resin having aromatic rings is a copolymer of styrene and divinylbenzene whose aromatic rings may have one or more substituents selected from the group consisting of halogen atoms and alkyl groups having 1 to 4 carbon atoms.

3. The method of claim 1, wherein a mixed solvent of water and alcohol is used as an eluent upon treating the solution with the nonpolar resin having aromatic rings.

4. The method of claim 1, wherein the solution contains a compound as an impurity which is unstable in a pH range lower than pH 7 or higher than 11.

5. The method of claim 1, wherein the solution contains a product obtained by reacting IHOG in the presence of an enzyme which is capable of catalyzing a reaction to generate monatin from IHOG.

6. The method of claim 5, wherein the enzyme reaction solution is an enzyme reaction solution obtained by aminating IHOG in the presence of aminotransferase and an amino group donor, the aminotransferase being capable of catalyzing a reaction to aminate IHOG to generate monatin.

7. The method of claim 6, wherein the amino group donor comprises at least one amino acid selected from the group consisting of alanine, glutamic acid and aspartic acid.

8. The method of claim 1, further comprising recovering monatin.

9. The method of claim 1, further comprising recovering IHOG.

10. The method of claim 1, further comprising recovering monatin and IHOG.

* * * * *